(12) United States Patent
Yamamoto et al.

(10) Patent No.: US 7,501,076 B2
(45) Date of Patent: Mar. 10, 2009

(54) FLUORESCENT DIKETOPYRROLOPYRROLES

(75) Inventors: Hiroshi Yamamoto, Nishinomiya (JP); Norihisa Dan, Yawata (JP)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 86 days.

(21) Appl. No.: 10/551,976

(22) PCT Filed: Apr. 1, 2004

(86) PCT No.: PCT/EP2004/050403

§ 371 (c)(1), (2), (4) Date: Jul. 13, 2006

(87) PCT Pub. No.: WO2004/090046

PCT Pub. Date: Oct. 21, 2004

(65) Prior Publication Data

US 2007/0010672 A1    Jan. 11, 2007

(30) Foreign Application Priority Data

Apr. 10, 2003    (EP) ................................. 03100972

(51) Int. Cl.
*C09K 11/06*    (2006.01)
*B32B 9/00*    (2006.01)
*C07D 401/14*    (2006.01)

(52) U.S. Cl. ............................ 252/301.16; 252/301.26; 428/690; 428/917; 546/256; 546/276.7

(58) Field of Classification Search ................ 548/453; 252/301.16, 301.26; 313/504, 506; 428/690, 428/917; 544/333; 546/256, 276.7
See application file for complete search history.

(56) References Cited

U.S. PATENT DOCUMENTS

| | | | | |
|---|---|---|---|---|
| 4,415,685 A | * | 11/1983 | Iqbal et al. ................ 524/92 |
| 4,585,878 A | | 4/1986 | Jost et al. .................. 548/453 |
| 4,931,566 A | | 6/1990 | Surber et al. ............... 548/453 |
| 5,354,869 A | * | 10/1994 | Langhals et al. ........... 548/453 |
| 5,571,359 A | * | 11/1996 | Kamen et al. .............. 156/233 |
| 5,646,299 A | | 7/1997 | Hao et al. .................. 548/453 |
| 5,969,154 A | | 10/1999 | Hao et al. .................. 548/453 |
| 6,413,655 B2 | | 7/2002 | Otani et al. ................ 428/690 |
| 6,451,459 B1 | | 9/2002 | Tieke et al. ................ 428/690 |
| 6,562,981 B2 | | 5/2003 | Otani et al. ................ 548/301.7 |
| 6,603,020 B1 | | 8/2003 | Moretti et al. .............. 548/453 |
| 2004/0009368 A1 | | 1/2004 | Otani et al. ................ 428/690 |
| 2004/0151944 A1 | | 8/2004 | Onikubo et al. ............ 428/690 |
| 2004/0180235 A1 | | 9/2004 | Yamamoto et al. .......... 428/690 |
| 2005/0008892 A1 | | 1/2005 | Yamamoto et al. .......... 428/690 |

FOREIGN PATENT DOCUMENTS

| | | |
|---|---|---|
| DE | 4 435 211 | 4/1995 |
| DE | 4435211 A1 * | 4/1995 |
| EP | 302 018 | 2/1989 |
| EP | 499 011 | 8/1992 |
| EP | 648 770 | 4/1995 |
| EP | 962 499 | 12/1999 |
| EP | 1 078 970 | 2/2001 |
| EP | 1 087 005 | 3/2001 |
| EP | 1 087 006 | 3/2001 |
| EP | 1087005 A1 * | 3/2001 |
| EP | 1087006 A1 * | 3/2001 |
| JP | 09-003448 A2 * | 1/1997 |
| WO | 90/01480 | 2/1990 |
| WO | 98/33862 | 8/1998 |
| WO | 03/048268 | 6/2003 |
| WO | 2004/009710 | 1/2004 |

OTHER PUBLICATIONS

Farnum et al, caplus an 1975:4148.*
David W. Oxtoby and Norman H. Nachtrieb, Principles of Modern Chemistry, 1990, Saunders College Publishing, 2nd Edition, p. 483.*
Patent abstracts of Japan vol. 015, No. 072 (C-0808; of JP 02296891).
English language abstract from the esp@cenet web site printed Nov. 23, 2005 of DE 4435211.
Patent abstracts of Japan vol. 018, No. 145 (C-1178; of JP 05320633).
Patent abstracts of Japan vol. 1997, No. 05 of JP 09003448.
English Language abstract No. 2002-210368[27] of JP 2001257077.
English Language abstract No. 2002-210369[27] of JP 2001257078.

* cited by examiner

*Primary Examiner*—Kamal A Saeed
*Assistant Examiner*—Kristin Bianchi
(74) *Attorney, Agent, or Firm*—Joseph C. Suhadolnik

(57) ABSTRACT

The present invention relates to fluorescent diketopyrrolopyrrole of the formula (I), a process for their preparation and their use for the preparation of inks, colorants, pigmented plastics for coatings, non-impact-printing material, color filters, cosmetics, polymeric ink particles, toners, as fluorescent tracers, in color changing media, in solid dye lasers and electroluminescent devices. A luminescent device comprising a composition according to the present invention is high in the efficiency of electrical energy utilisation and high in luminance.

12 Claims, No Drawings

FLUORESCENT DIKETOPYRROLOPYRROLES

The present invention relates to fluorescent diketopyrrolopyrroles (DPPs) of the formula I

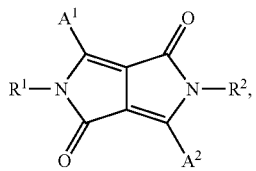

a process for their preparation and their use for the preparation of inks, colorants, pigmented plastics for coatings, non-impact-printing material, color filters, cosmetics, polymeric ink particles, toners, as fluorescent tracers, in color changing media, dye lasers and electroluminescent devices. A luminescent device comprising a compound according to the present invention is high in the efficiency of electrical energy utilisation and high in luminance.

EP-A-648770 relates to DPPs containing carbamate groups and their use as fluorescence dyestuff. In Examples 6 and 9 the following DPP compounds are disclosed:

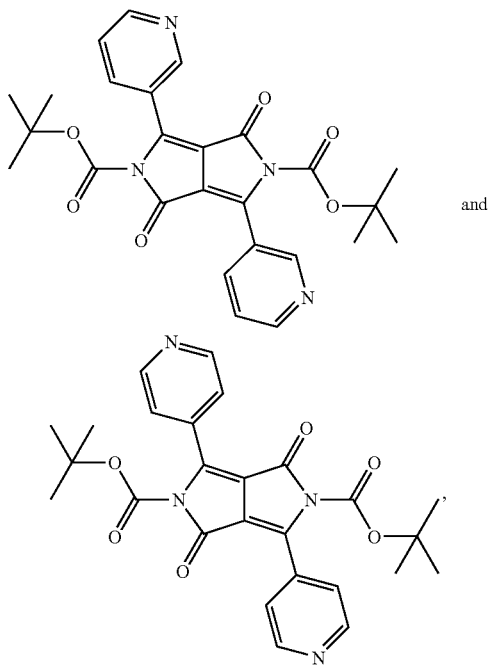

respectively.

WO90/01480 relates to substances, among others DPP compounds, with at least two different coloured forms, one of which can be converted to the other by supplying energy and their use in storage media. In Examples 10 and 11 the following DPP compounds are disclosed:

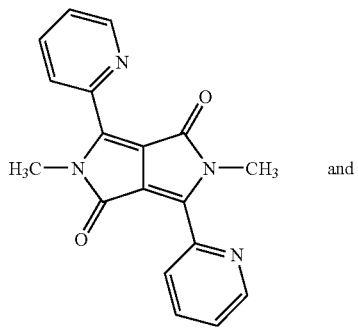

and

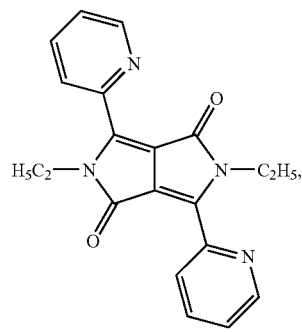

respectively.

It is presently common to prepare organic electroluminescent ("EL") devices which contain an organic fluorescent substance by a vacuum evaporation process, e.g. described in Appl. Phys. Lett., 51, 913 (1987). In general, two types of such vacuum evaporation processes are applied according to the constitution of light emitting material: a one-component type process and a two-component type (or "Host-Guest type" or "binary systems") process (e.g. described in J. Appl. Phys., 65, 3610 (1989)).

JP-A2 2,296,891 (Ricoh) claims an electroluminescent element comprising a positive electrode, a negative electrode and one organic compound layer or a plurality of organic compound layers held between the positive and negative electrodes, but no hole transporting substance. At least one layer of said organic compound layers is a layer containing a pyrrolopyrrole compound represented by the following formula II″

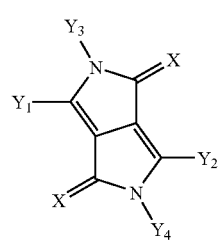

wherein $Y_1$ and $Y_2$ independently from each other represent a substituted or unsubstituted alkyl, cycloalkyl or aryl group, $Y_3$ and $Y_4$ independently represent a hydrogen atom or a substituted or unsubstituted alkyl or aryl group, and X represents an oxygen or a sulfur atom. Four compounds are mentioned explicitly, namely wherein X stands for oxygen In all cases, and wherein (a) $Y_3=Y_4$=methyl and $Y_1=Y_2$=p-tolyl, (b) $Y_3=Y_4$=methyl and $Y_1=Y_2$=hydrogen, (c) $Y_3=Y_4$=hydrogen and $Y_1=Y_2$=p-tolyl, and (d) $Y_3=Y_4=Y_1$=hydrogen and $Y_2$=p-chlorophenyl. No emission is observed, if DPP II″ is used alone, i.e. without the addition of tris(8-hydroxyquinolinato) aluminium ("Alq₃").

JP-A2 5,320,633 (Sumitomo) claims an organic EL device having a light emitting layer comprising a light emitting material in an amount of 0.005 to 15 parts by weight of a DPP of the formula

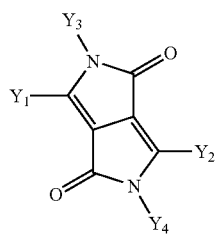

between a pair of electrodes, wherein at least one electrode being transparent or semi-transparent, wherein $Y_1$ and $Y_2$ independently of each other stand for a $C_6$-$C_{14}$-aryl group or a $C_6$-$C_{12}$heterocyclic group, such as thienyl, 2-pyridyl, 3-pyridyl and 4-pyridyl, and $Y_3$ and $Y_4$ independently of each other stand for a hydrogen atom, a $C_1$-$C_{12}$-alkyl group or a $C_6$-$C_{14}$aryl group. Although the main claim is silent about the use of $Alq_3$, it is clear from the specification and the examples, especially from comparative example 2, that $Alq_3$ is an essential feature in the claimed EL element or device.

JP-A2 9003448 (Toyo) describes an organic EL element having between a pair of electrodes a luminous layer containing a DPP-compound as electron-transporting material or an organic compound thin film layer including a luminous layer and an electron-injecting layer wherein the electron-injecting layer contains a DPP compound as the electron-transporting material. The following three heteroarylpyrrolopyrroles are explicitly mentioned:

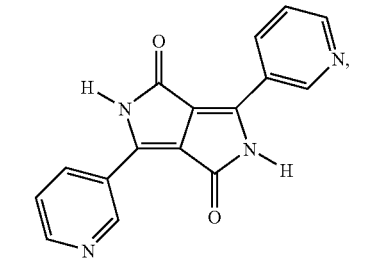

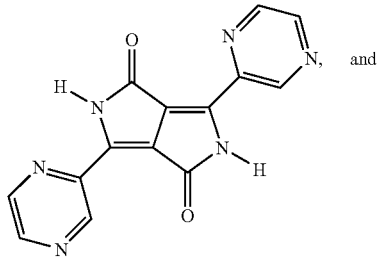

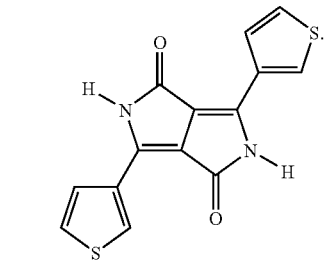

The disadvantage of the claimed EL devices is that according to the examples always $Alq_3$ and a phenanthrene diamine (as hole-injecting material) have to be used.

EP-A-499,011 describes electroluminescent devices comprising DPP-compounds of the formula

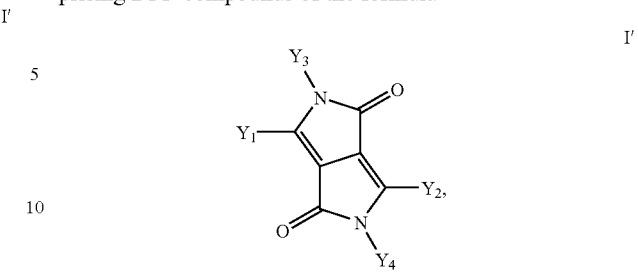

wherein $Y_1$ and $Y_2$ can be a substituted or unsubstituted phenyl group, a 3-pyridyl- or 4-pyridylgroup and $Y_3$ and $Y_4$ independently of each other stand for a hydrogen atom, a $C_1$-$C_{18}$-alkyl group, an $C_3$-$C_{18}$alkenyl group and the double bond not being the $C_1$-position. In example 1 and 7 the following DPP compounds are explicitly mentioned

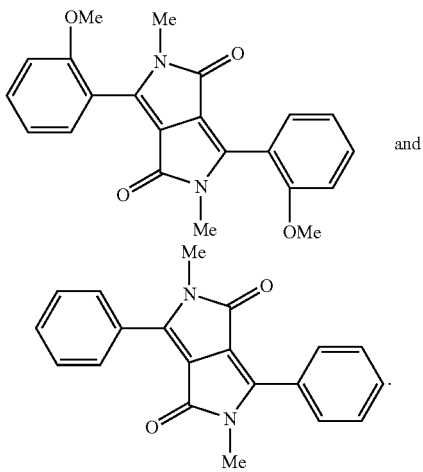

WO98/33862 describes the use of the DPP-compound of formula IV'

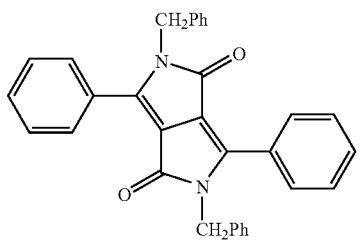

as a guest molecule in electroluminescent devices.

EP-A-1087005 relates to fluorescent N-substituted diketopyrrolopyrroles ("DPPs") of the formula I'

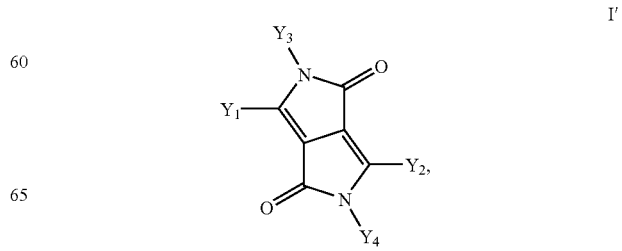

characterized in that $Y^1$ and $Y^2$ are derived from the following groups:

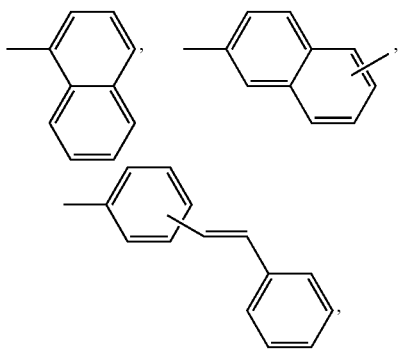

example

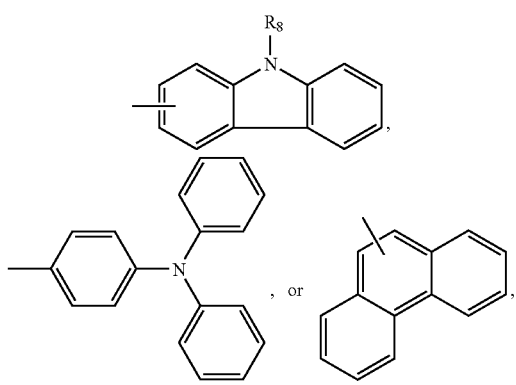

which can be substituted or unsubstituted.

EP-A-1087006 relates to an electroluminescent device comprising in this order (a) an anode, (b) a hole transporting layer, (c) a light-emitting layer, (d) optionally an electron transporting layer and (e) a cathode and a light-emitting substance, wherein the light-emitting substance is a diketopyrrolopyrrole ("DPP") represented by formula I'.

WO03/002672 relates to diketopyrrolopyrroles of formula I' characterized in that $Y^1$ and $Y^2$ are derived from the following 1-naphthyl group:

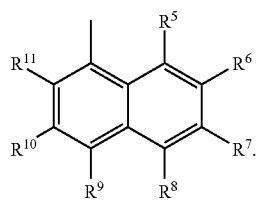

PCT/EP03/00650 discloses EL devices comprising a DPP guest chromophore of formula IV and a DPP host chromophore of formula II (see below).

EP-A-1,253,151 discloses EL devices comprising at least one of
(a) a DPP derivative and an organic fluorescent material having a fluorescent peak wavelength in the range of 580 to 720 nm and
(b) a pyrromethene metal complex (see also JP2001 257077, JP2001 257078, and JP2001 297881 (Toray))

WO03/048268 relates to compositions for EL elements, comprising a compound having a perylene ring and a compound having a DPP skeleton. The following three heteroarylpyrrolopyrroles are explicitly mentioned:

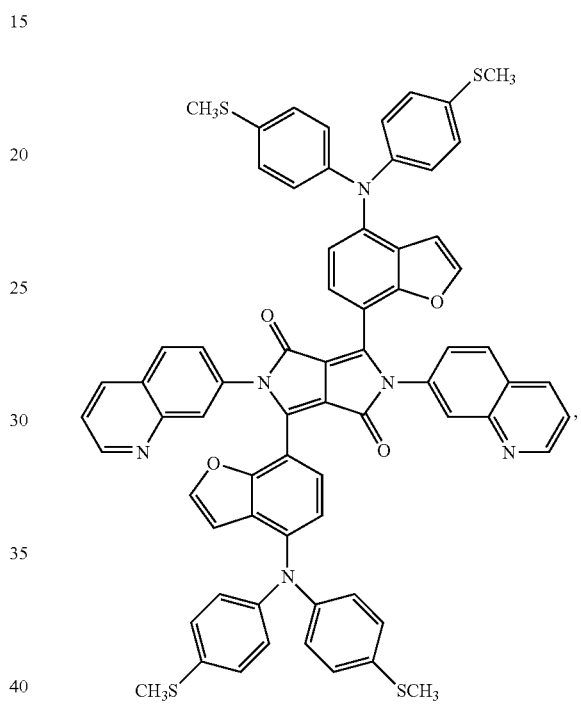

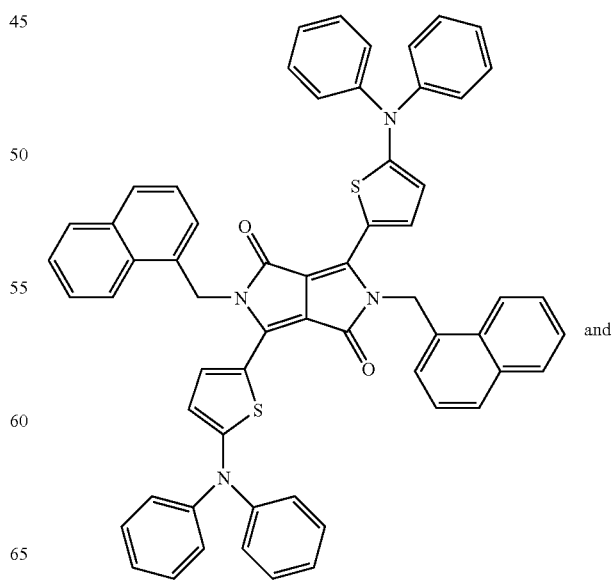

and

-continued

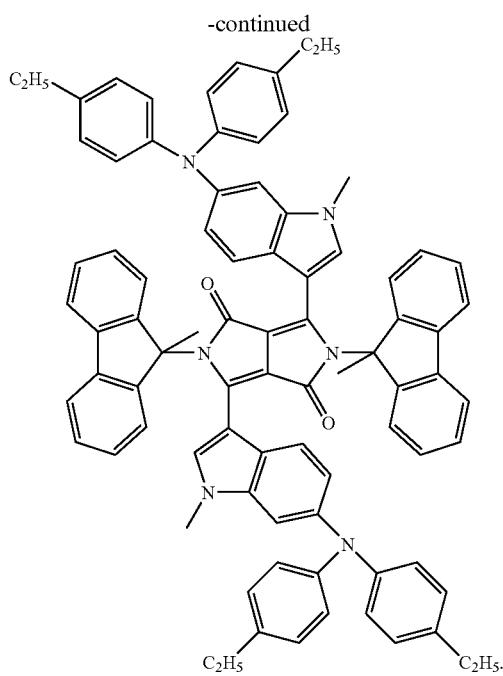

Surprisingly, it was found that luminescent devices, which are high in the efficiency of electrical energy utilisation and high in luminance, can be obtained if specific DPP compounds or specific combinations of DPP compounds are used, especially as light emitting substances.

Accordingly, the present invention relates to fluorescent diketopyrrolopyrrole of the formula I

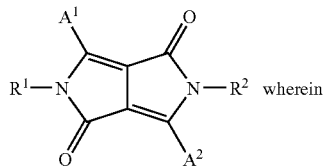

wherein $R^1$ and $R^2$ may be the same or different and are selected from a $C_1$-$C_{25}$alkyl group, which can be substituted by fluorine, chlorine or bromine, an allyl group, which can be substituted one to three times with $C_1$-$C_4$alkyl, a cycloalkyl group, or a cycloalkyl group, which can be condensed one or two times by phenyl which can be substituted one to three times with $C_1$-$C_4$-alkyl, halogen, nitro or cyano, an alkenyl group, a cycloalkenyl group, an alkynyl group, a haloalkyl group, a haloalkenyl group, a haloalkynyl group, a ketone or aldehyde group, an ester group, a carbamoyl group, a ketone group, a silyl group, a siloxanyl group, $A^3$ or —$CR^3R^4$—$(CH_2)_m$-$A^3$ wherein $R^3$ and $R^4$ independently from each other stand for hydrogen or $C_1$-$C_4$alkyl, or phenyl which can be substituted one to three times with $C_1$-$C_4$alkyl, $A^3$ stands for aryl or heteroaryl, in particular phenyl or 1- or 2-naphthyl which can be substituted one to three times with $C_1$-$C_8$alkyl and/or $C_1$-$C_8$alkoxy, and m stands for 0, 1, 2, 3 or 4, $A^1$ and $A^2$ are independently of each other a group comprising a five-membered heterocyclic ring, containing one to three heteroatoms selected from the group of nitrogen, oxygen and sulfur, or a six-membered heterocyclic ring, containing one to three heteroatoms selected from the group of nitrogen, oxygen and sulfur, wherein, if $A^1$ and $A^2$ are a single five- or six-membered heterocyclic ring of formula

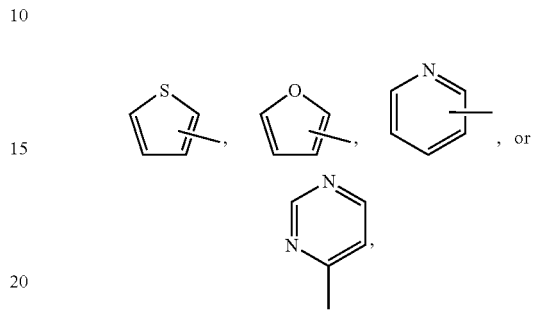

said heterocyclic ring is substituted by at least a group selected from a $C_1$-$C_{25}$alkyl group, a cycloalkyl group, an aralkyl group, an alkenyl group, a cycloalkenyl group, an alkynyl group, a hydroxyl group, a mercapto group, an alkoxy group, an alkylthio group, an aryl ether group, an aryl thioether group, an aryl group, a heterocyclic group, a halogen atom, a haloalkyl group, a haloalkenyl group, a haloalkynyl group, a cyano group, an aldehyde group, a carboxyl group, an ester group, a carbamoyl group, a nitro group, a silyl group, a siloxanyl group, a substituted or unsubstituted vinyl group, a group $NR^8R^9$, wherein $R^8$ and $R^9$ independently of each other stand for a hydrogen atom, an alkyl group, a cycloalkyl group, an aryl group, a heteroaryl group, a heterocyclic group, an aralkyl group, or $R^8$ and $R^9$ together with the nitrogen atom to which they are bonded form a five or six membered heterocyclic ring, which can be condensed by one or two optionally substituted phenyl groups, wherein the heterocyclic ring is directly bonded to the DPP basis unit, especially

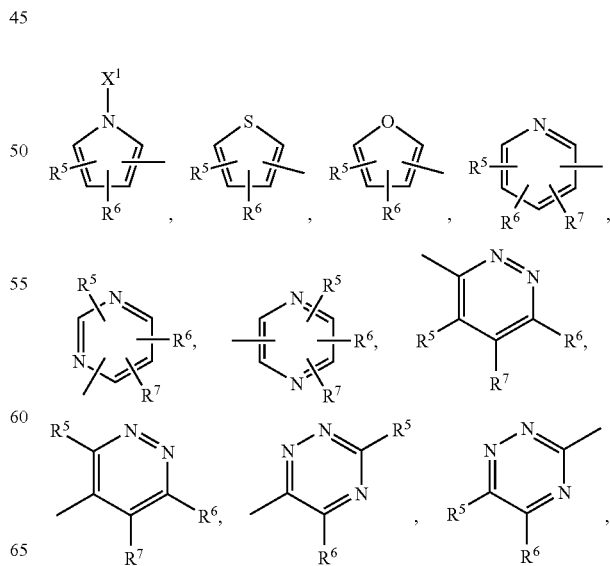

-continued

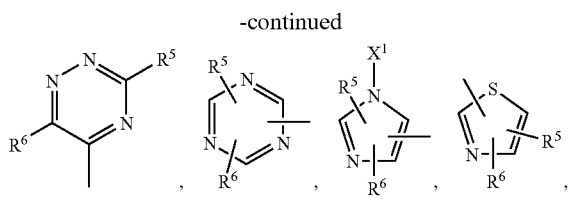
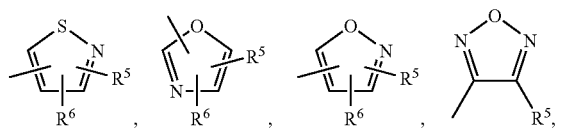
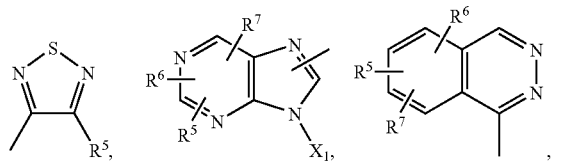
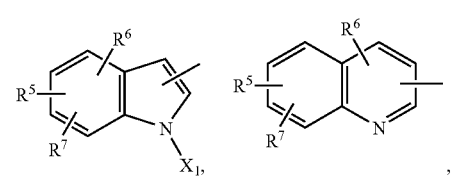
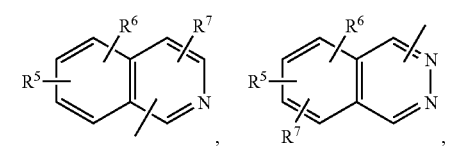
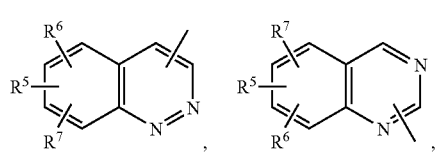
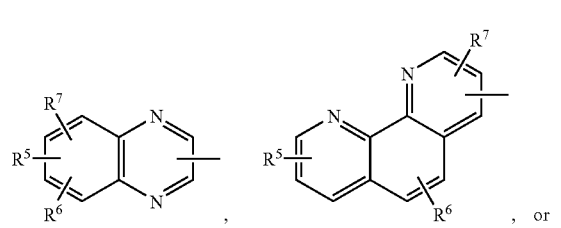
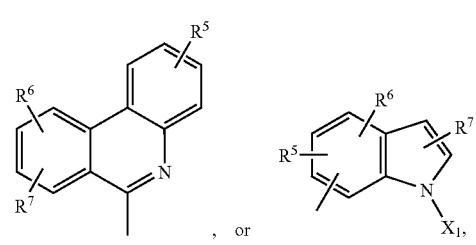

-continued

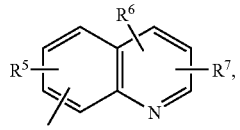

$A^1$ and $A^2$ are independently of each other a group

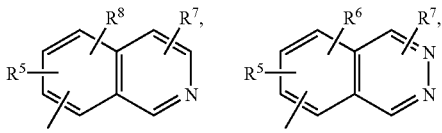
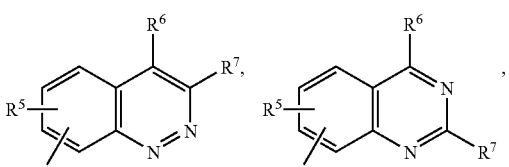
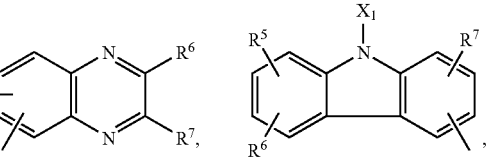
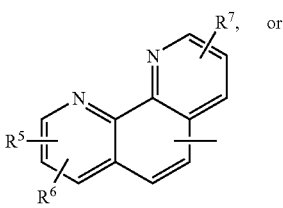

, or

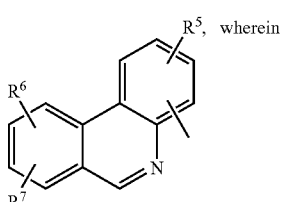

, wherein

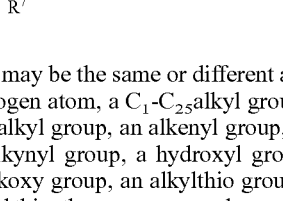

$R^5$, $R^6$, and $R^7$ may be the same or different and are selected from a hydrogen atom, a $C_1$-$C_{25}$alkyl group, a cycloalkyl group, an aralkyl group, an alkenyl group, a cycloalkenyl group, an alkynyl group, a hydroxyl group, a mercapto group, an alkoxy group, an alkylthio group, an aryl ether group, an aryl thioether group, an aryl group, a heterocyclic group, a halogen atom, a haloalkyl group, a haloalkenyl group, a haloalkynyl group, a cyano group, an aldehyde group, a carboxyl group, an ester group, a carbamoyl group, a nitro group, a silyl group, a siloxanyl group, a substituted or unsubstituted vinyl group, a group $NR^8R^9$, wherein $R^8$ and $R^9$ independently of each other stand for a hydrogen atom, an alkyl group, a cycloalkyl group, an aryl group, a heteroaryl group, a heterocyclic group, an aralkyl group, or $R^8$ and $R^9$ together with the nitrogen atom to which they are bonded form a five or six membered heterocyclic ring, which can be condensed by one or two optionally substituted phenyl groups, or at least two adjacent substituents $R^5$ to $R^7$ form an aromatic or aliphatic fused ring system, and $X^1$ is a hydrogen atom, a $C_1$-$C_{25}$alkyl group, a cycloalkyl group, an aralkyl group, an aryl group, or a heterocyclic group, with the proviso, that the following compounds are

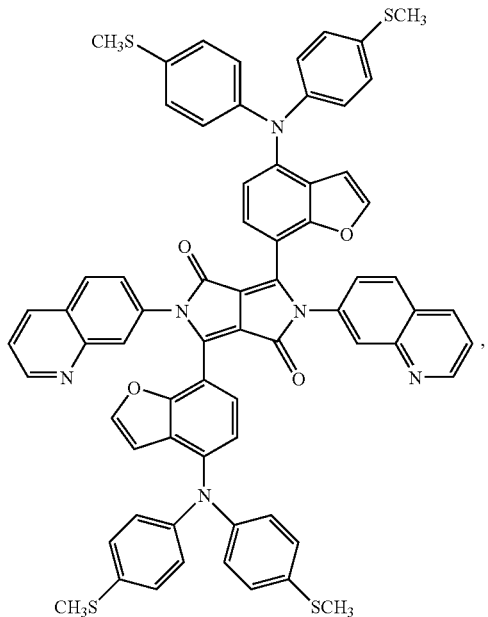

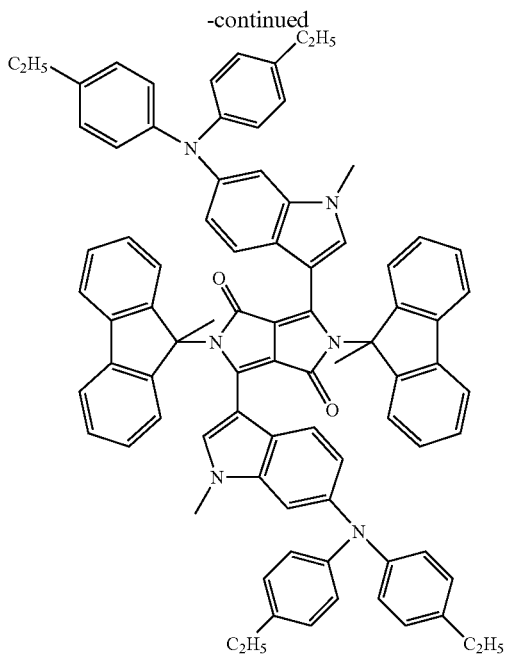

are excluded.

$A^1$ and $A^2$ can be different, but are preferably the same. If $A^1$ and $A^2$ are a group of formula

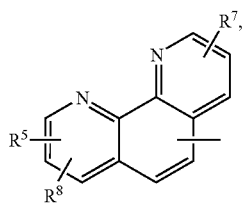

they are preferably a group of formula

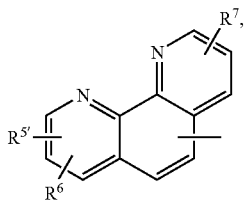

wherein $R^{5'}$ is $R^5$ except hydrogen.

In a preferred embodiment of the present invention at least one of the groups $R^5$, $R^6$, and $R^7$ is different from a hydrogen atom, if $A^1$ and $A^2$ are a single five- or six-membered heterocyclic ring, containing one heteroatom selected from the group of nitrogen, oxygen and sulfur.

In another preferred embodiment of the present invention at least one of the groups $R^5$, $R^6$ and $R^7$ is different from a hydrogen atom.

Preferably $R^1$ and $R^2$ independently from each other are selected from $C_1$-$C_{14}$alkyl, $C_5$-$C_{12}$-cycloalkyl, especially cyclohexyl, which can be substituted one to three times with $C_1$-$C_8$alkyl and/or $C_1$-$C_8$alkoxy, or $C_5$-$C_{12}$-cycloalkyl, especially cyclohexyl, which can be condensed one or two times

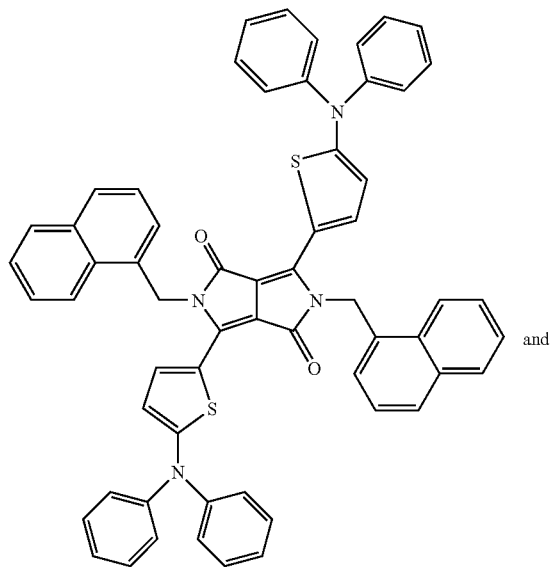

and by phenyl, which can be substituted one to three times with $C_1$-$C_4$-alkyl, halogen, nitro or cyano, phenyl or 1- or 2-naphthyl which can be substituted one to three times with $C_1$-$C_8$alkyl and/or $C_1$-$C_8$alkoxy, or —$CR^3R^4$—$(CH_2)_m$-$A^3$ wherein $R^3$ and $R^4$ stand for hydrogen, $A^3$ stands for phenyl or 1- or 2-naphthyl, which can be substituted one to three times with $C_1$-$C_8$alkyl and/or $C_1$-$C_8$alkoxy, and m stands for 0 or 1.

Preferably $A^1$ and $A^2$ independently from each other are selected from

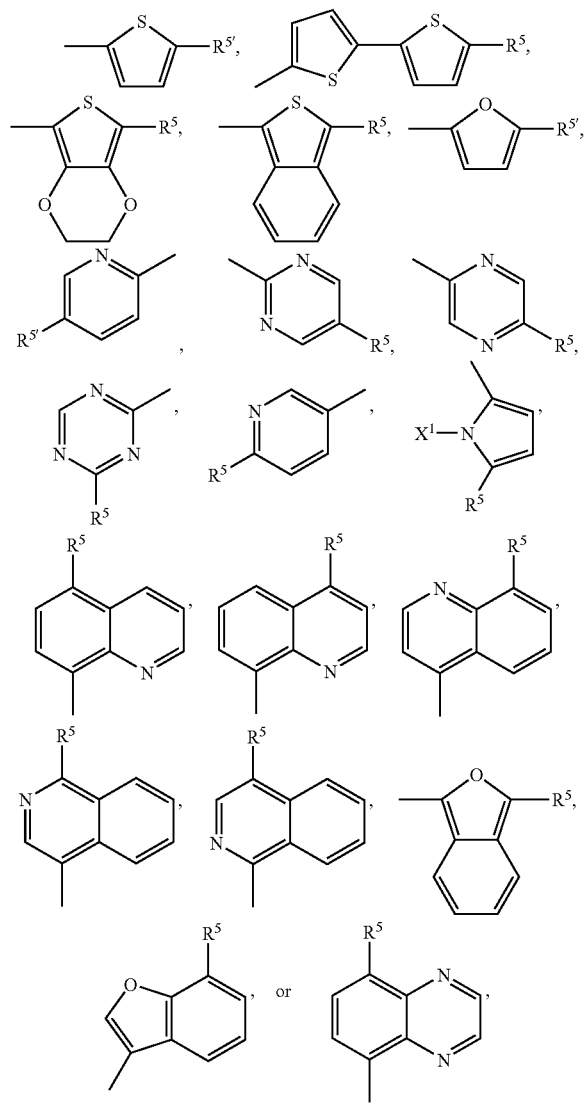

wherein
$R^5$ is a hydrogen atom, a $C_1$-$C_{12}$alkyl group, a $C_1$-$C_8$alkoxy group, a group of formula

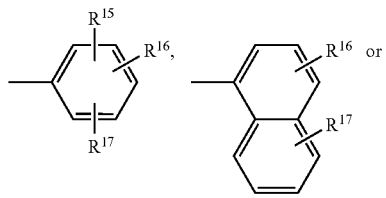

or a group —$NR^8R^9$, wherein $R^8$ and $R^9$ independently from each other stand for $C_1$-$C_8$alkyl group, $A^1$, such as

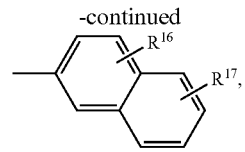

especially

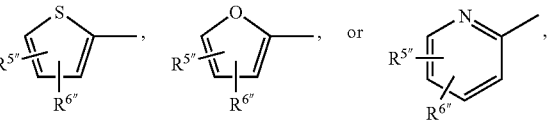

or $R^8$ and $R^9$ together with the nitrogen atom to which they are bonded form a five or six membered heterocyclic ring, such as

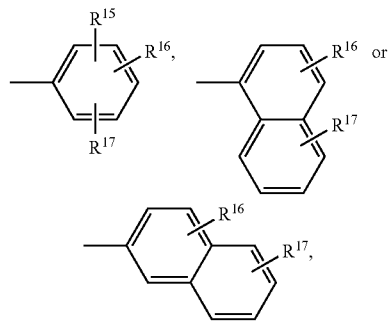

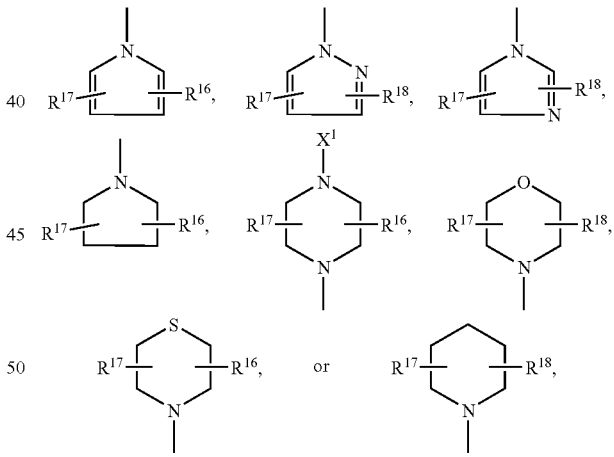

which can be condensed by one or two optionally substituted phenyl groups, such as

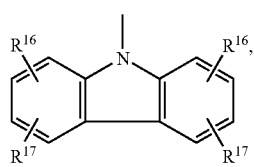

wherein $R^{15}$, $R^{16}$ and $R^{17}$ independently from each other stands for hydrogen, $C_1$-$C_8$-alkyl, $C_1$-$C_8$-alkoxy, or phenyl, $R^{5'}$ is $R^5$, except hydrogen, $R^{5''}$ and $R^{6''}$ independently from each other stands for hydrogen, $C_1$-$C_8$-alkyl or $C_1$-$C_8$-alkoxy, and $X^1$ stands for hydrogen, or $C_1$-$C_8$-alkyl.
The following diketopyrrolopyrroles are preferred:
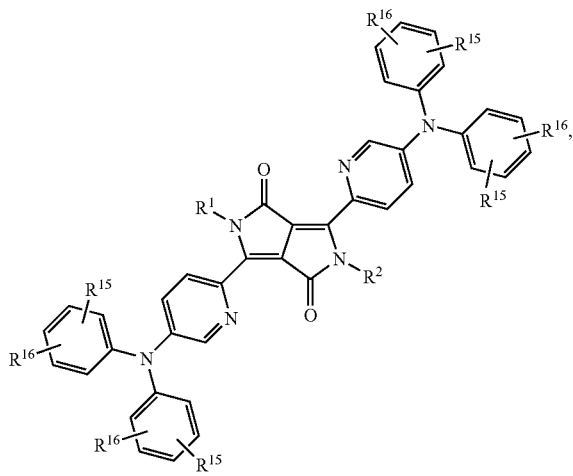
especially
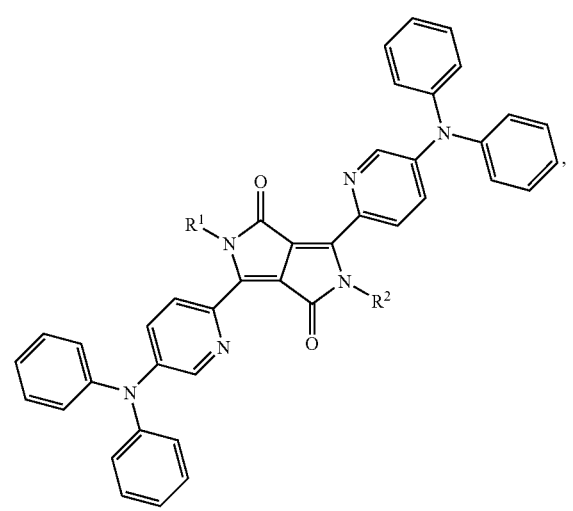
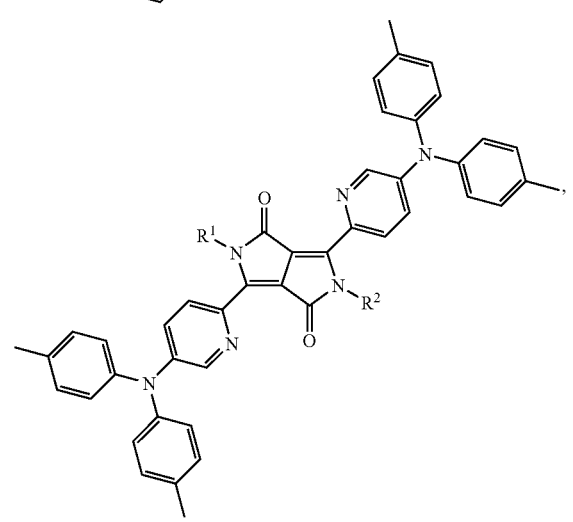
-continued
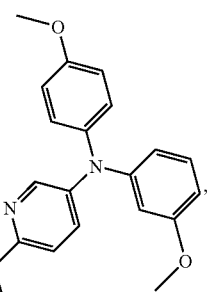
especially
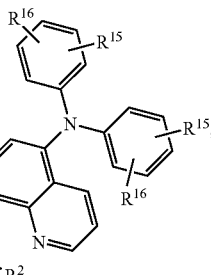

-continued
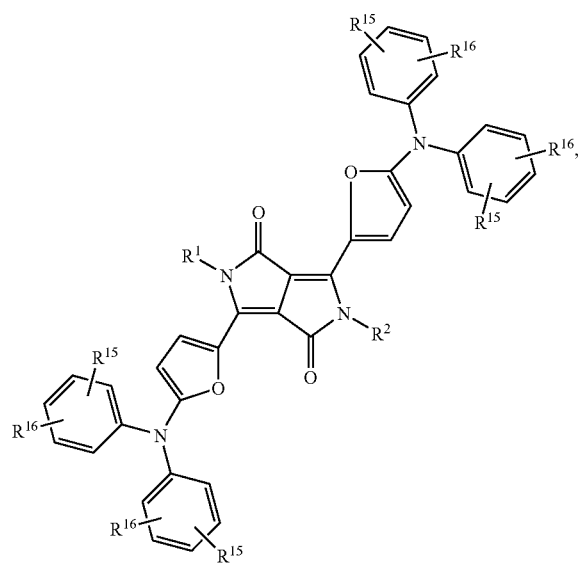
especially
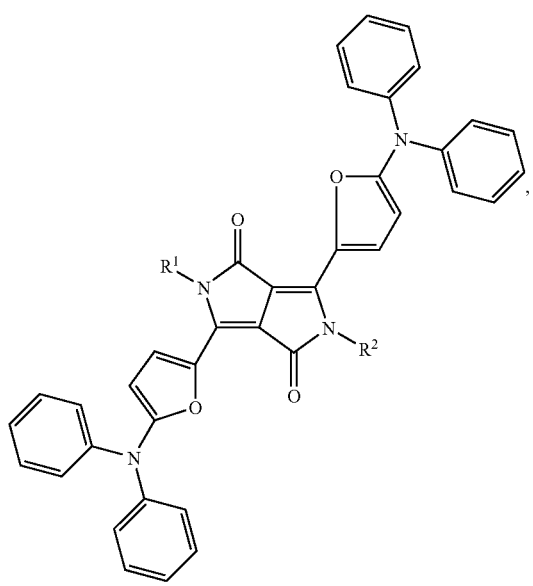
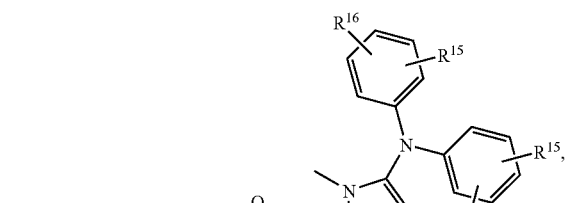
especially

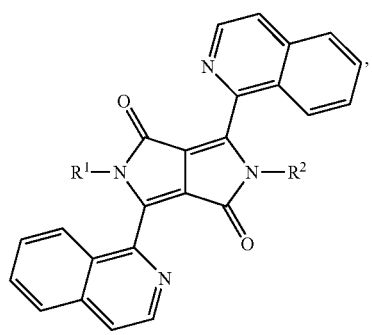
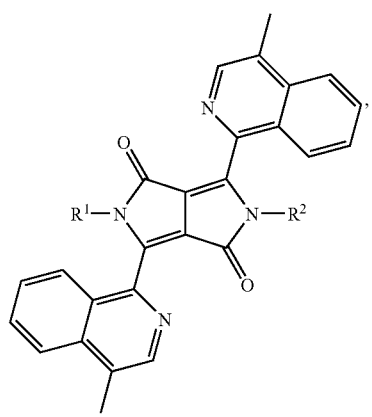
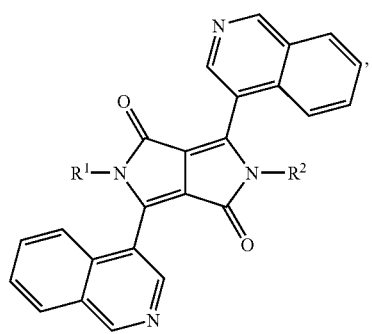
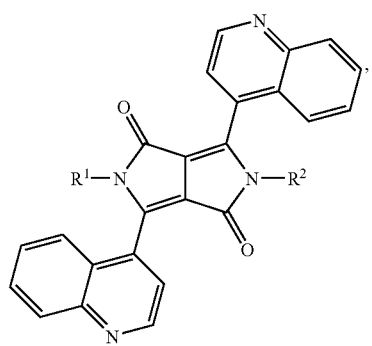
-continued
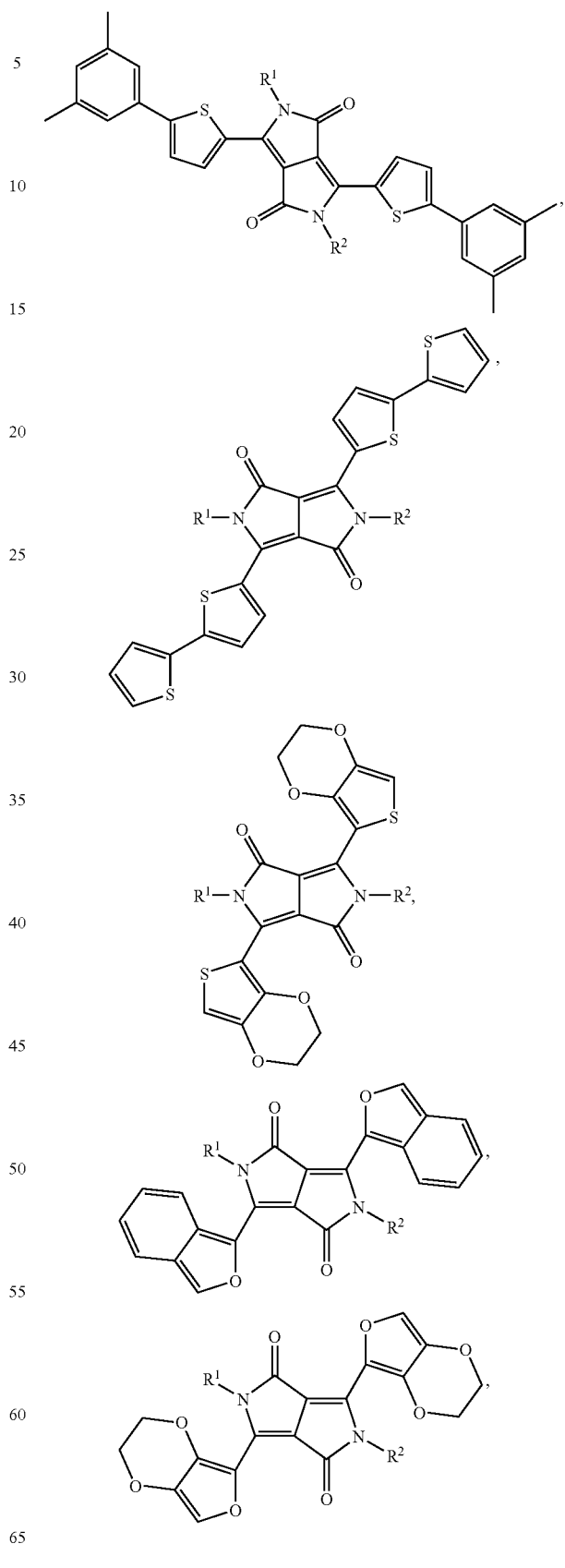

-continued
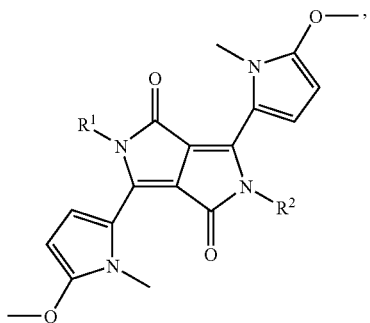
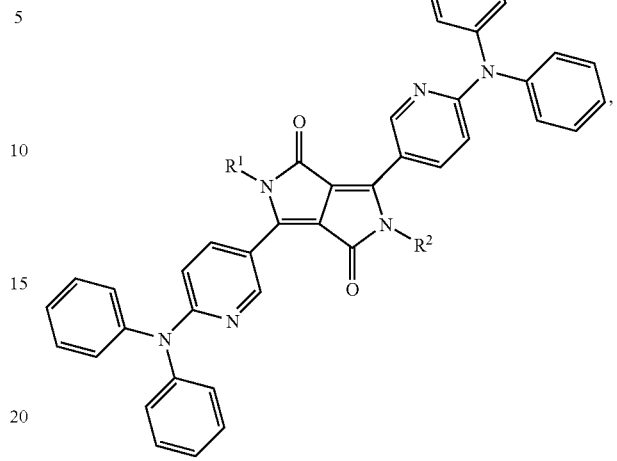
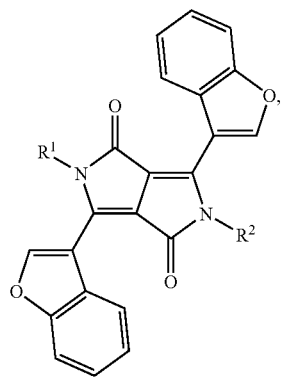
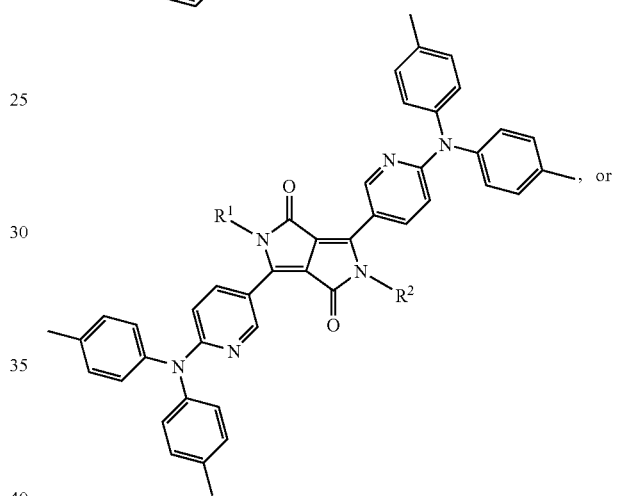
especially
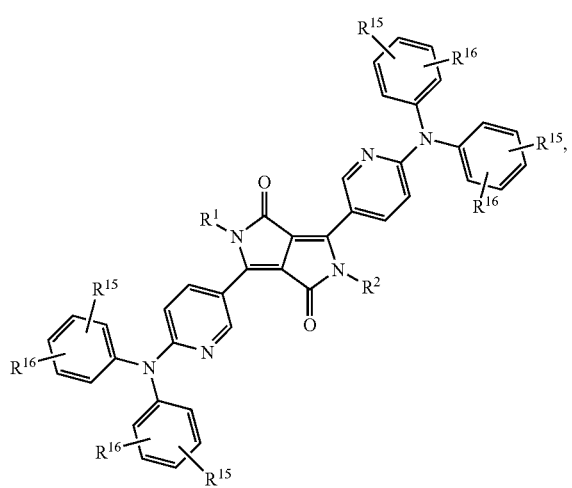
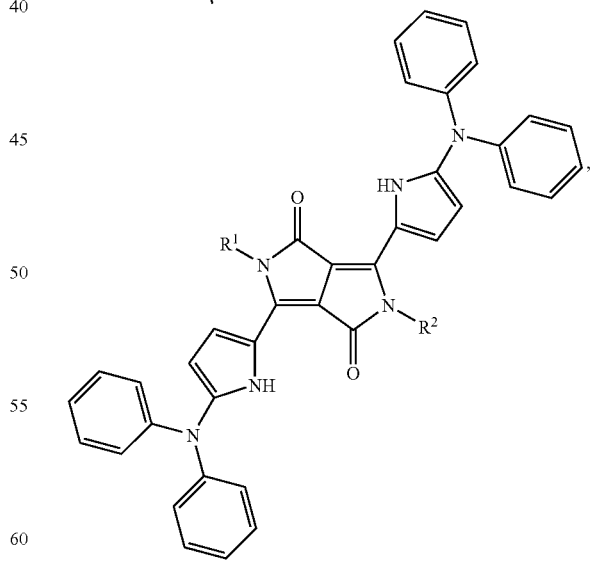
wherein $R^1$ and $R^2$ are independently of each other a $C_1$-$C_{12}$alkyl group, such as methyl, ethyl, n-propyl, isopropyl, n-butyl, sec.-butyl, isobutyl, tert.-butyl, n-pentyl, 2-pentyl, 3-pentyl, 2,2-dimethylpropyl, n-hexyl, n-heptyl, n-octyl, 1,1,3,3-tetramethylbutyl and 2-ethylhexyl, n-nonyl, n-decyl, n-undecyl, n-dodecyl, a $C_5$-$C_7$cycloalkyl group, which can be substituted one to three times with $C_1$-$C_8$alkyl and/or $C_1$-$C_8$alkoxy, or which can be condensed one or two times by optionally substituted phenyl, especially

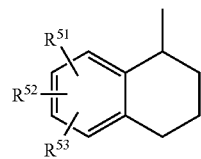 or 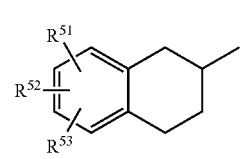, wherein $R^{51}$, $R^{52}$ and $R^{53}$ are independently of each other hydrogen, $C_1$-$C_8$-alkyl, $C_1$-$C_8$-alkoxy, halogen and cyano, or a $C_7$-$C_{14}$aralkyl group, such as —$CR^3R^4$—$(CH_2)_m$-$A^3$ wherein $R^3$ and $R^4$ stand for hydrogen, $A^3$ stands phenyl, biphenyl or 1- or 2-naphthyl which can be substituted one to three times with $C_1$-$C_8$alkyl and/or $C_1$-$C_8$alkoxy, and m stands for 0 or 1, such as $C_1$-$C_8$alkylphenyl, di($C_1$-$C_8$alkyl) phenyl, in particular 3-methylphenyl, 4-methylphenyl, 3,5-dimethylphenyl, 3,5-di-tert.-butylphenyl and 2,5- and 2,6-diisopropylphenyl, wherein the following diketopyrrolopyrroles are especially preferred:

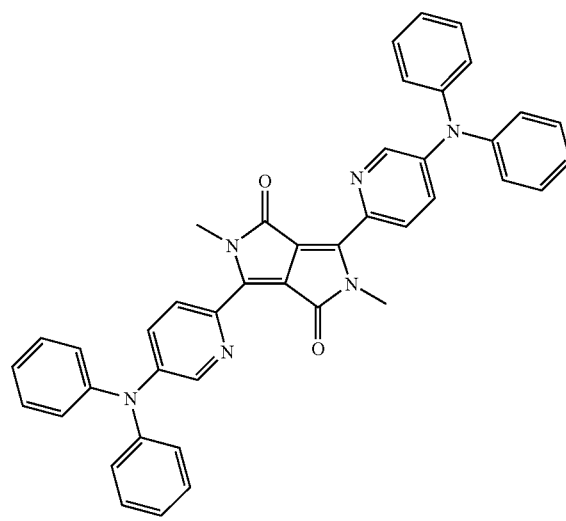

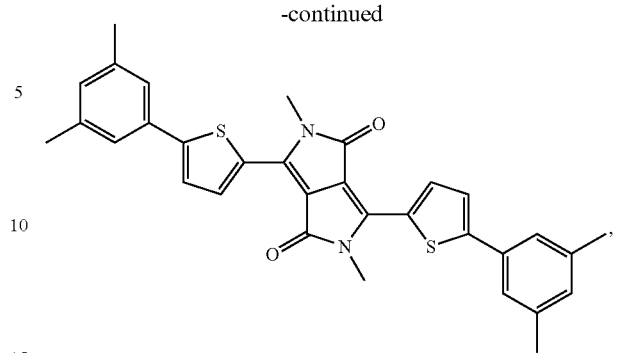

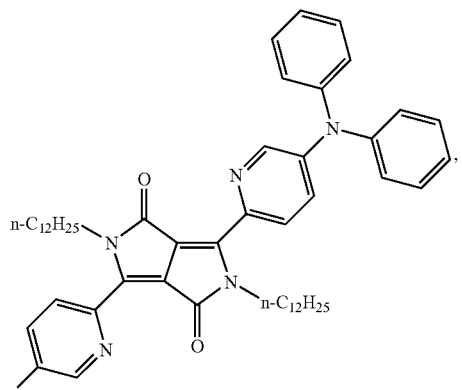

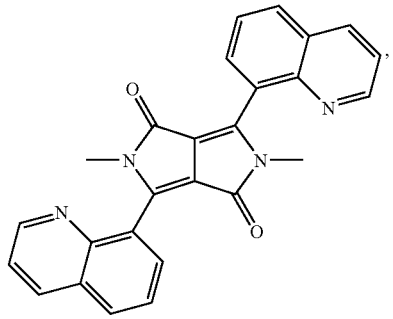

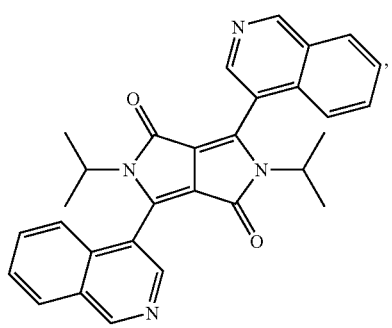

-continued
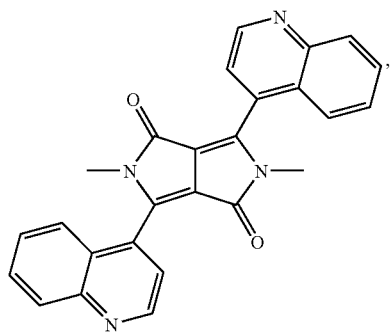
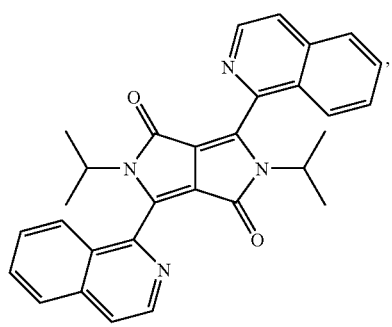
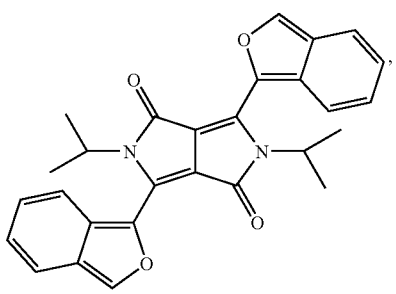
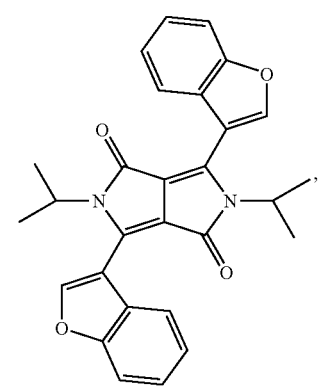
-continued
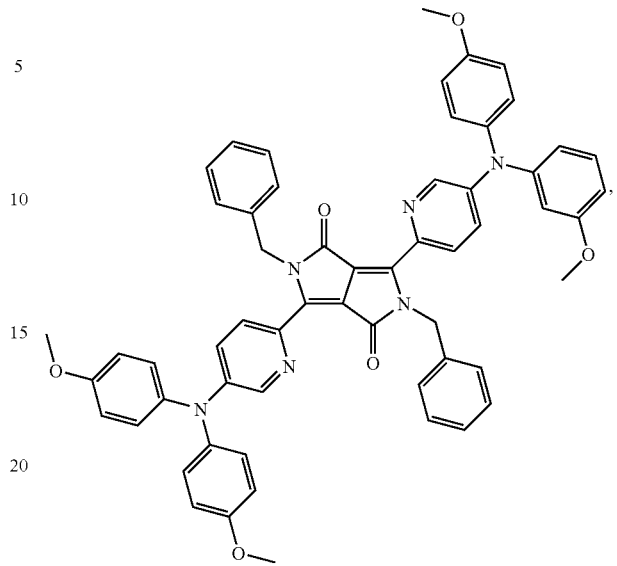
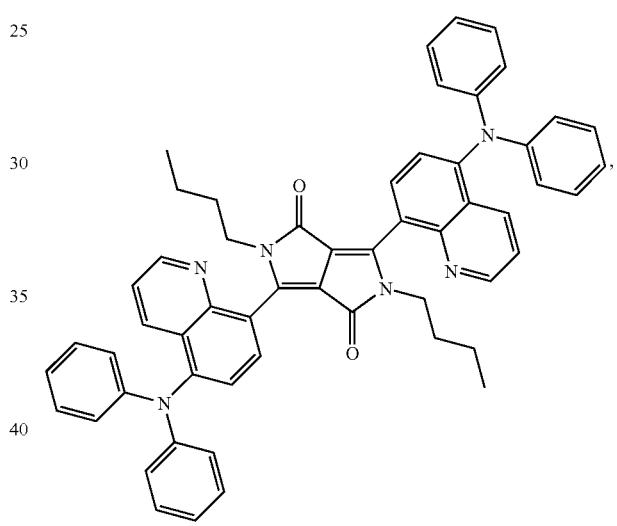
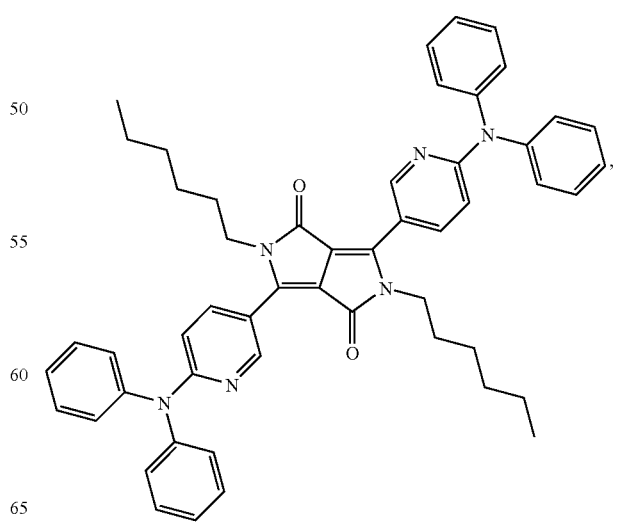

-continued
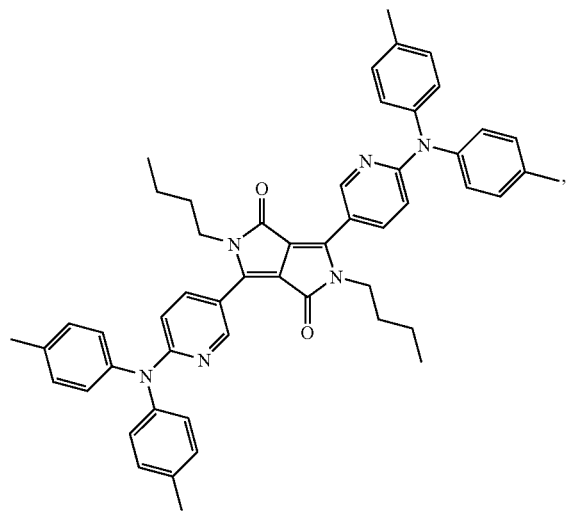
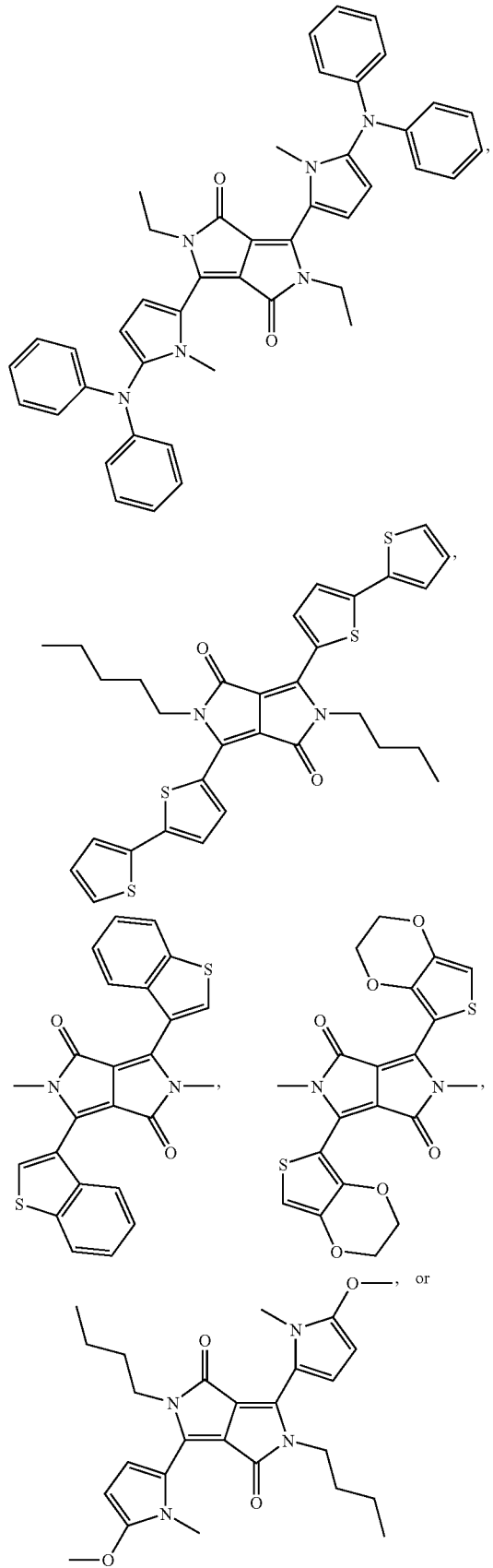

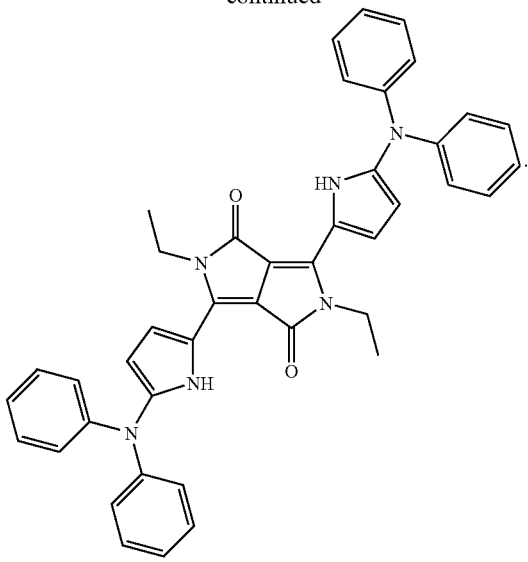

A further preferred embodiment of the present invention is directed to compositions comprising a guest chromophore and a host chromophore, wherein the absorption spectrum of the guest chromophore overlaps with the fluorescence emission spectrum of the host chromophore, wherein the host chromophore is a diketopyrrolopyrrole having a photoluminescence emission peak at 500 to 720 nm, preferably 520 to 630 nm, most preferred 540 to 600 nm and wherein the host chormophore and/or the guest chromophore is a diketopyrrrolopyrrole of formula I. That means, specific host choromophores of formula I can be used in combination with specific guest choromophores of formula I or guest choromophores of formula IV, and specific guest choromophores of formula I can be used In combination with specific host choromophores of formula II.

In one embodiment of the present invention, the compositions comprise a host chromophore, which is a diketopyrrolopyrrole having a photoluminescence emission peak at 500 to 720 nm, preferably 520 to 630 nm, most preferred 540 to 600 nm and the guest chromophore is a diketopyrrolopyrrole of formula I.

In this embodiment the host chromophore is preferably a diketopyrrolopyrrole ("DPP") represented by formula II

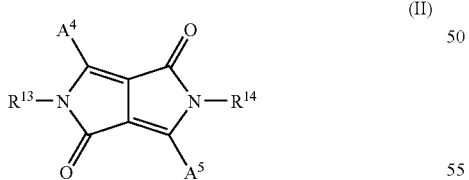

(II)

wherein $R^{13}$ and $R^{14}$ independently from each other stand for $C_1$-$C_{25}$-alkyl, which can be substituted by fluorine, chlorine or bromine, $C_5$-$C_{12}$-cycloalkyl or $C_5$-$C_{12}$cycloalkyl which can be condensed one or two times by phenyl which can be substituted one to three times with $C_1$-$C_4$-alkyl, halogen, nitro or cyano, silyl, $A^6$ or —$CR^{11}R^{12}$—$(CH_2)_m$-$A^6$, wherein $R^{11}$ and $R^{12}$ independently from each other stand for hydrogen, fluorine, chlorine, bromine, cyano or $C_1$-$C_4$alkyl, which can be substituted by fluorine, chlorine or bromine, or phenyl which can be substituted one to three times with $C_1$-$C_4$alkyl, $A^6$ stands for phenyl or 1- or 2-naphthyl which can be substituted one to three times with $C_1$-$C_8$alkyl, $C_1$-$C_8$alkoxy, halogen, nitro, cyano, phenyl, which can be substituted with $C_1$-$C_8$alkyl or $C_1$-$C_8$alkoxy one to three times, —$NR^{23}R^{24}$, wherein $R^{23}$ and $R^{24}$ represent hydrogen, $C_1$-$C_{25}$-alkyl, $C_5$-$C_{12}$-cycloalkyl or $C_6$-$C_{24}$-aryl, in particular phenyl or 1- or 2-naphthyl which can be substituted one to three times with $C_1$-$C_8$alkyl, $C_1$-$C_8$alkoxy, halogen or cyano, or phenyl, which can be substituted with $C_1$-$C_8$alkyl or $C_1$-$C_8$alkoxy one to three times, and m stands for 0, 1, 2, 3 or 4, $A^4$ and $A^5$ independently from each other stand for

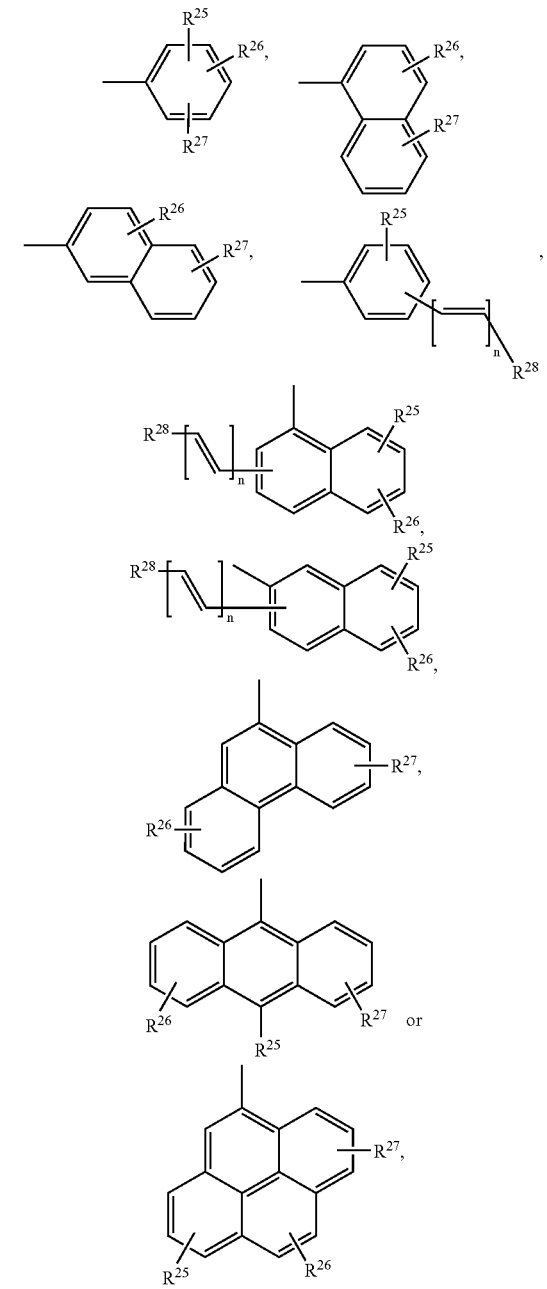

wherein $R^{25}$, $R^{26}$, $R^{27}$ independently from each other stands for hydrogen, $C_1$-$C_{25}$-alkyl, —$CR^{11}R^{12}$—$(CH_2)_m$-$A^6$, cyano, halogen, —$OR^{29}$, —$S(O)_pR^{30}$, or phenyl, which can be substituted one to three times with $C_1$-$C_8$alkyl or $C_1$-$C_8$alkoxy, wherein $R^{29}$ stands for $C_1$-$C_{25}$-alkyl, $C_5$-$C_{12}$- cycloalkyl, —CR$^{11}$R$^{12}$—(CH$_2$)$_m$-Ph, C$_6$-C$_{24}$-aryl, or a saturated or unsaturated heterocyclic radical comprising five to seven ring atoms, wherein the ring consists of carbon atoms and one to three hetero atoms selected from the group consisting of nitrogen, oxygen and sulfur, R$^{30}$ stands for C$_1$-C$_{25}$-alkyl, C$_5$-C$_{12}$-cycloalkyl, —CR$^{11}$R$^{12}$—(CH$_2$)$_m$-Ph, R$^{28}$ stands for C$_2$-C$_{20}$-heteroaryl, C$_6$-C$_{24}$-aryl, p stands for 0, 1, 2 or 3, m and n stands for 0, 1, 2, 3 or 4.

R$^{13}$ and R$^{14}$ independently of each other stand, preferably, for C$_1$-C$_8$alkyl, C$_5$-C$_{12}$-cycloalkyl, which can be substituted one to three times with C$_1$-C$_8$alkyl and/or C$_1$-C$_8$alkoxy, phenyl or 1- or 2-naphthyl which can be substituted one to three times with C$_1$-C$_8$alkyl and/or C$_1$-C$_8$alkoxy, or —CR$^{11}$R$^{12}$—(CH$_2$)$_m$-A$^6$ wherein R$^{11}$ and R$^{12}$ stand for hydrogen, A$^6$ stands for phenyl or 1- or 2-naphthyl, which can be substituted one to three times with C$_1$-C$_8$alkyl and/or C$_1$-C$_8$alkoxy, and m stands for 0 or 1.

A$^4$ and A$^5$ independently from each other stand, preferably, for

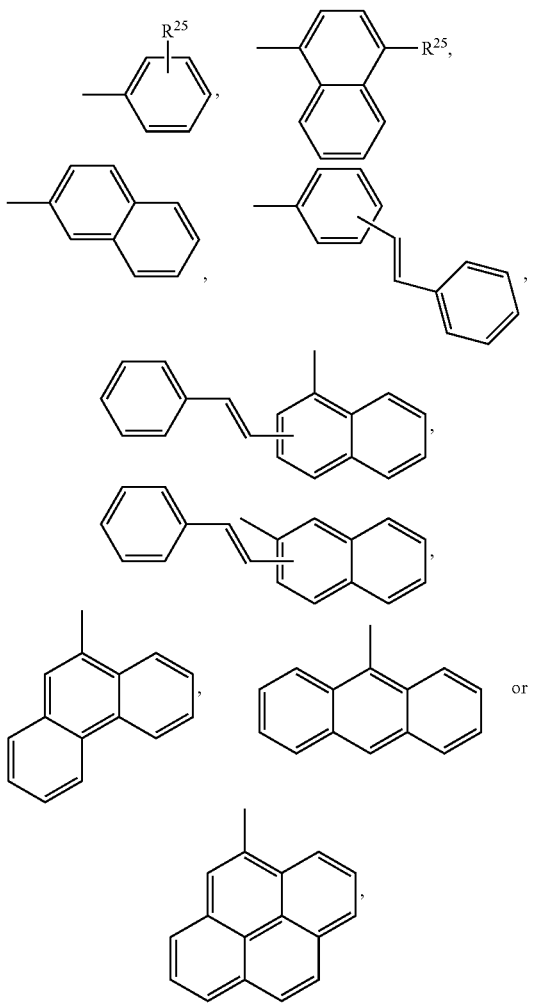

wherein R$^{25}$ is C$_1$-C$_8$-alkyl, phenyl, 1- or 2-naphthyl.

In another preferred embodiment of the present invention, the compositions comprise a host chromophore, which is a diketopyrrolopyrrole of formula I, and a guest chromophore, which is a diketopyrrolopyrrole of formula IV

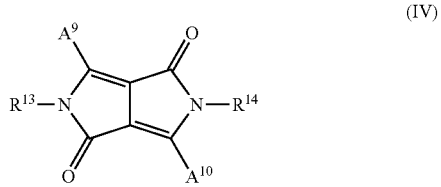

wherein R$^{13}$ and R$^{14}$ are as defined above, and

A$^9$ and A$^{10}$ independently from each other stand for

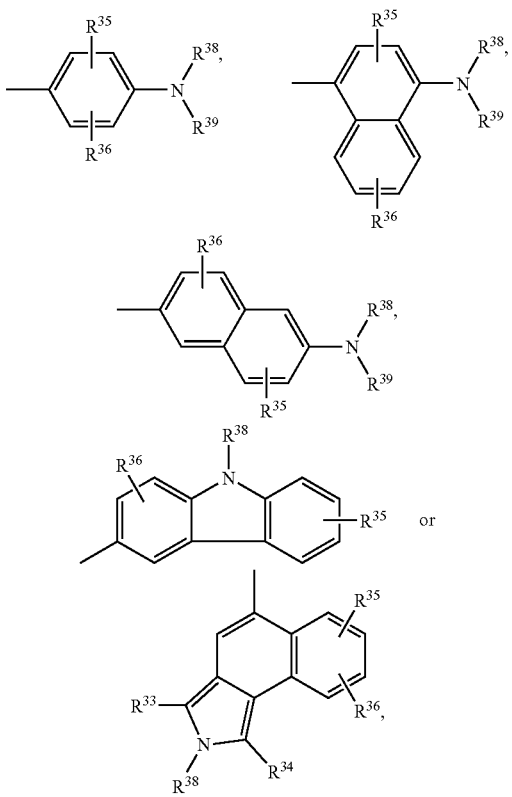

R$^{35}$ and R$^{36}$ independently from each other stands for hydrogen, C$_1$-C$_{25}$-alkyl, C$_1$-C$_{25}$-alkoxy, —CR$^{11}$R$^{12}$—(CH$_2$)$_m$-A$^6$, cyano, halogen, —OR$^{40}$, —S(O)$_p$R$^{41}$, or phenyl, which can be substituted one to three times with C$_1$-C$_8$alkyl or C$_1$-C$_8$alkoxy, wherein R$^{40}$ stands for C$_1$-C$_{25}$-alkyl, C$_5$-C$_{12}$-cycloalkyl, —CR$^{11}$R$^{12}$—(CH$_2$)$_m$-Ph, C$_6$-C$_{24}$-aryl, or a saturated or unsaturated heterocyclic radical comprising five to seven ring atoms, wherein the ring consists of carbon atoms and one to three hetero atoms selected from the group consisting of nitrogen, oxygen and sulfur, R$^{41}$ stands for C$_1$-C$_{25}$-alkyl, C$_5$-C$_{12}$-cycloalkyl, —CR$^{11}$R$^{12}$—(CH$_2$)$_m$-Ph, p stands for 0, 1, 2 or 3, m and n stands for 0, 1, 2, 3 or 4, R$^{38}$ and R$^{39}$ independently from each other stand for hydrogen, C$_1$-C$_{25}$-alkyl, C$_5$-C$_{12}$-cycloalkyl, —CR$^{11}$R$^{12}$—(CH$_2$)$_m$-A$^6$, C$_6$-C$_{24}$-aryl, in particular A$^6$, or a saturated or unsaturated heterocyclic radical comprising five to seven ring atoms, wherein the ring consists of carbon atoms and one to three hetero atoms selected from the group consisting of nitrogen, oxygen and sulfur, such as A$^1$, especially

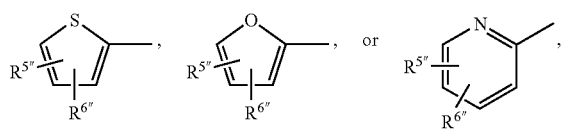

wherein R$^{5''}$ and R$^{6''}$ independently from each other stands for hydrogen, C$_1$-C$_8$alkyl or C$_1$-C$_8$-alkoxy, or R$^{38}$ and R$^{39}$ together with the nitrogen atom to which they are bonded form a five or six membered heterocyclic ring which can be condensed by one or two optionally substituted phenyl groups, such as

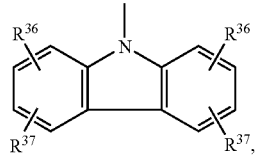

and R$^{33}$ and R$^{34}$ independently from each other stand for hydrogen and C$_6$-C$_{24}$-aryl, in particular phenyl, wherein R$^{11}$, R$^{12}$ and A$^6$ are as defined above.

If A$^9$ and A$^{10}$ independently from each other stand for a group of the formula

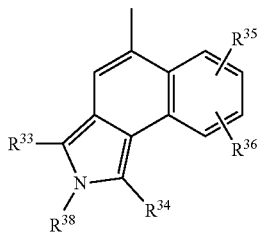

R$^{35}$ and R$^{36}$ are preferably hydrogen, R$^{38}$ is preferably C$_1$-C$_6$alkyl or phenyl and R$^{33}$ and R$^{34}$ are preferably hydrogen or phenyl.

If A$^9$ and A$^{10}$ independently from each other stand for a group of the formula

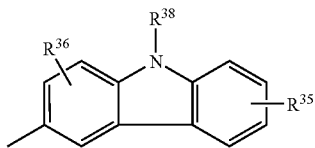

R$^{35}$ and R$^{36}$ are preferably hydrogen and R$^{38}$ is preferably C$_1$-C$_6$alkyl or phenyl.

In particular A$^9$ and A$^{10}$ independently of each other stand for

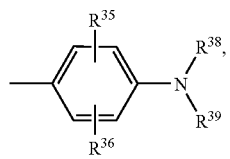 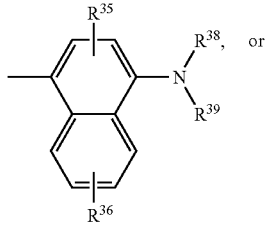

-continued

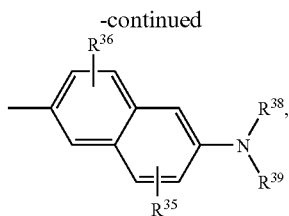

wherein R$^{35}$ and R$^{36}$ independently from each other stand for hydrogen, C$_1$-C$_8$-alkyl, C$_1$-C$_8$-alkoxy, —CR$^{11}$R$^{12}$—(CH$_2$)$_m$-A$^6$, cyano, chloro, —OR$^{40}$, or phenyl, which can be substituted one to three times with C$_1$-C$_8$alkyl or C$_1$-C$_8$alkoxy, wherein R$^{40}$ stands for C$_1$-C$_8$-alkyl, or C$_6$-C$_{24}$-aryl, such as phenyl, 1-naphthyl or 2-naphthyl, R$^{11}$ and R$^{12}$ are hydrogen or C$_1$-C$_4$alkyl, m is 0 or 1, A$^6$ is phenyl, 1-naphthyl or 2-naphthyl, R$^{38}$ and R$^{39}$ independently from each other stand for hydrogen, C$_1$-C$_8$-alkyl, C$_5$-C$_{12}$-cycloalkyl, in particular cyclohexyl, —CR$^{11}$R$^{12}$—(CH$_2$)$_m$-A$^6$, C$_6$-C$_{24}$-aryl, such as phenyl, 1-naphthyl, 2-naphthyl, 4-biphenyl, phenanthryl, terphenyl, pyrenyl, 2- or 9-fluorenyl or anthracenyl, preferably C$_6$-C$_{12}$aryl such as phenyl, 1-naphthyl, 2-naphthyl, 4-biphenyl, which may be unsubstituted or substituted, especially by one, or two C$_1$-C$_8$-alkyl, or C$_1$-C$_8$alkoxy groups, in particular A$^6$, or a saturated or unsaturated heterocyclic radical comprising five to seven ring atoms, wherein the ring consists of carbon atoms and one to three hetero atoms selected from the group consisting of nitrogen, oxygen and sulfur, especially A$^1$, or R$^{38}$ and R$^{38}$ together with the nitrogen atom to which they are bonded form a five or six membered heterocyclic ring which can be condensed by one or two optionally substituted phenyl groups, such as

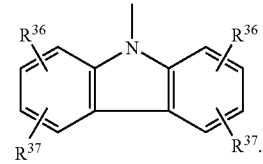

In particular groups of the following formula are preferred

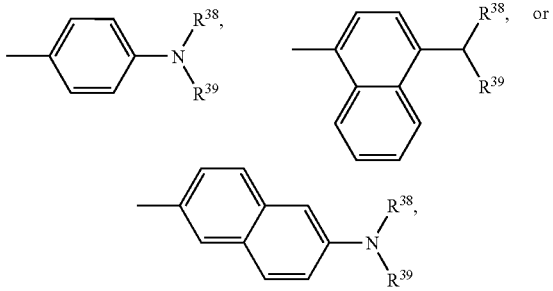

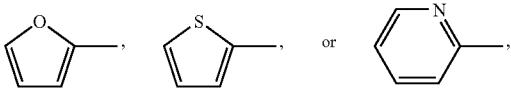

wherein R$^{38}$ and R$^{39}$ independently of each other stand for A$^1$, especially or a group of the formula

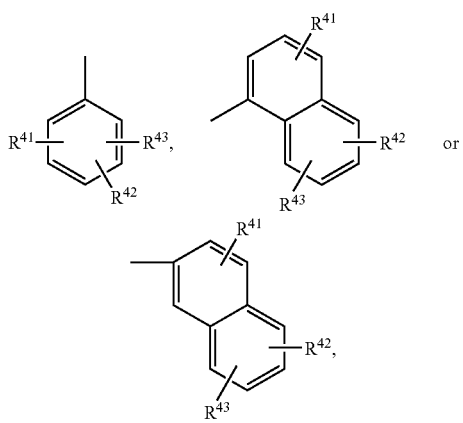

wherein $R^{41}$, $R^{42}$ and $R^{43}$ are independently of each other hydrogen, $C_1$-$C_8$alkyl, a hydroxyl group, a mercapto group, $C_1$-$C_8$alkoxy, $C_1$-$C_8$alkylthio, halogen, halo-$C_1$-$C_8$alkyl, a cyano group, an aldehyde group, a ketone group, a carboxyl group, an ester group, a carbamoyl group, an amino group, a nitro group, a silyl group or a siloxanyl group, or $R^{38}$ and $R^{39}$ together with the nitrogen atom to which they are bonded form the following condensed ring system

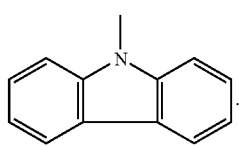

Preferably $R^{41}$, $R^{42}$ and $R^{43}$ are independently of each other hydrogen, $C_1$-$C_8$alkyl, $C_1$-$C_8$alkoxy or $C_1$-$C_8$alkylthio.

The weight ratio of the host chromophore to the guest chromophore is in general 50:50 to 99.99:0.01, preferably 90:10 to 99.99:0.01, more preferably 95:5 to 99.9:0.1, most preferred 98:2 to 99.9:0.1.

Compounds of formula I, wherein $A^1$ and $A^2$ independently from each other are selected from

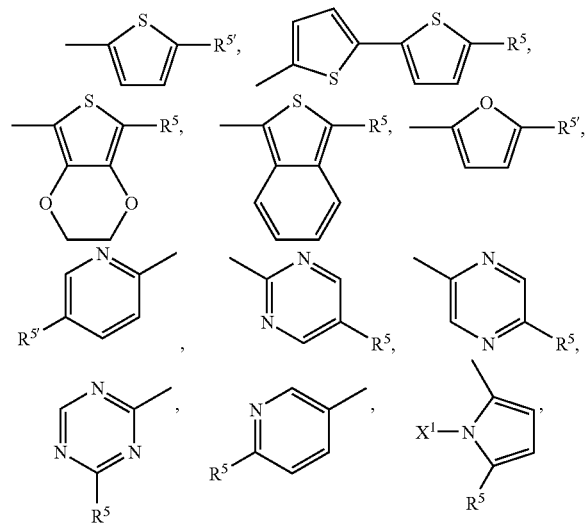

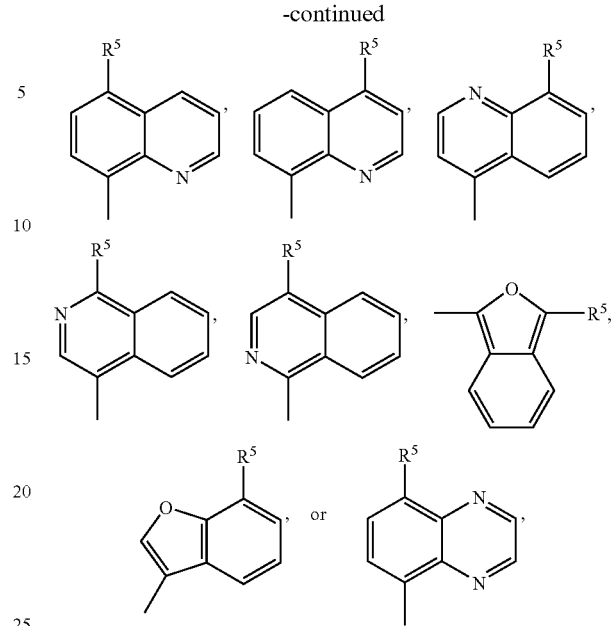

wherein $R^5$ is a hydrogen atom, a $C_1$-$C_{12}$alkyl group, a $C_1$-$C_8$alkoxy group, a group of formula

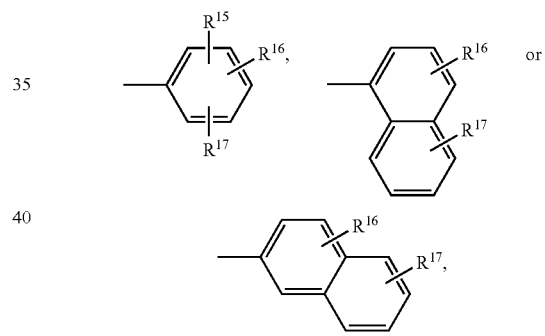

wherein $R^{15}$, $R^{16}$ and $R^{17}$ independently from each other stands for hydrogen, $C_1$-$C_8$-alkyl or $C_1$-$C_8$-alkoxy $R^{5'}$ is $R^5$, except hydrogen, and $X^1$ stands for hydrogen, or $C_1$-$C_8$-alkyl; are preferred as host compounds.

Particularly preferred as host chromophores are the DPP compounds represented by the formula I or II, which are listed below:

| Compound (of formula II) | $A^4 = A^5$ | $R^{13} = R^{14}$ |
|---|---|---|
| H-1 | —⌬—CH₃ | H₃C—CH(—⌬) |

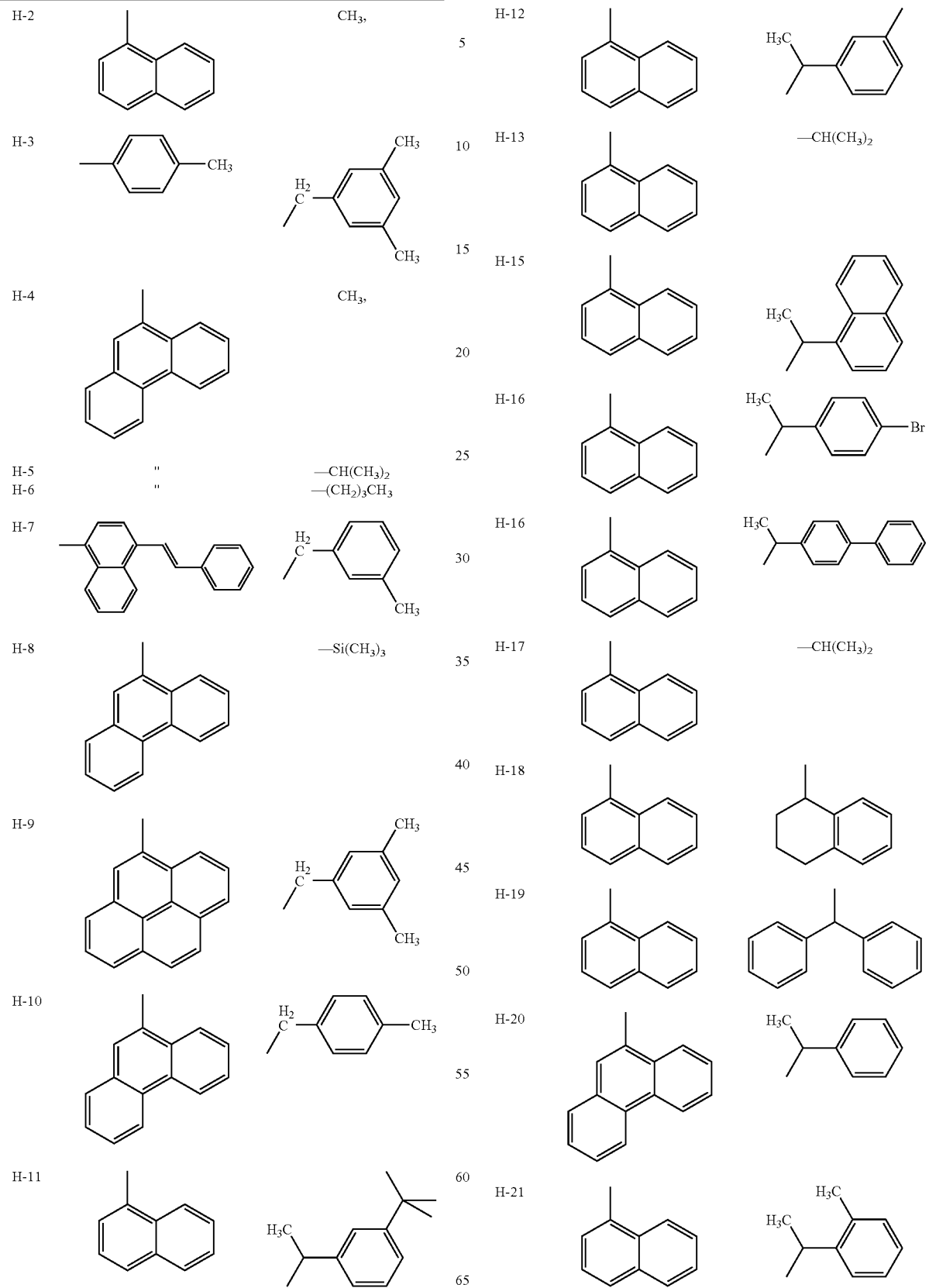

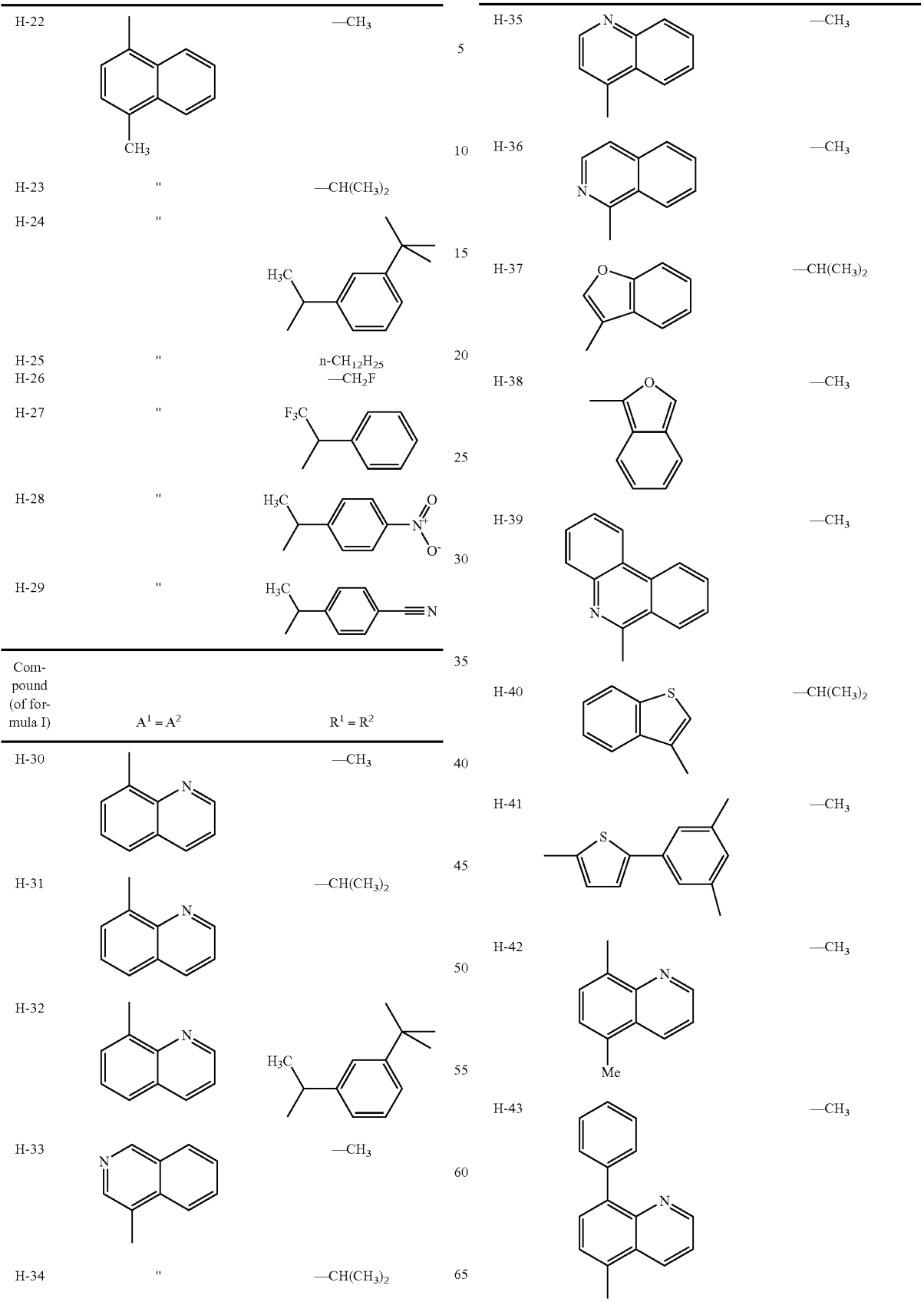

-continued

| | | |
|---|---|---|
| H-44 | [1-Me-isoquinolin-4-yl] | —CH₃ |
| H-45 | [1-Me-4-Me-isoquinolin-yl] | —CH₃ |
| H-46 | [5,8-diMe-quinoxalin-yl] | —CH₃ |
| H-47 | [1-phenyl-4-Me-isoquinolin-yl] | —CH₃ |

Compounds of formula I, wherein $A^1$ and $A^2$ independently from each other are selected from

[structures: thiophene-R⁵; thiophene-phenyl with R¹⁵, R¹⁶; bithiophene-R⁵; EDOT-R⁵; benzo-thiophene-R⁵; furan-R⁵; pyridine; pyrimidine-R⁵; pyrazine-R⁵; triazine-R⁵; pyridine-R⁵]

-continued

[structures: N-substituted pyrrole with X¹, R⁵; quinoline-R⁵ variants; isoquinoline-R⁵; benzofuran-R⁵; quinoxaline-R⁵], wherein $R^5$ is a group —NR⁸R⁹, wherein $R^8$ and $R^9$ independently from each other stand for $C_1$-$C_8$-alkyl, $A^1$, such as

[thiophene, furan, pyridine structures with R⁵″, R⁶″], or especially

[phenyl with R¹⁵, R¹⁶, R¹⁷; naphthalene structures with R¹⁶, R¹⁷], or $R^8$ and $R^9$ together with the nitrogen atom to which they are bonded form a five or six membered heterocyclic ring which can be condensed by one or two optionally substituted phenyl groups, such as

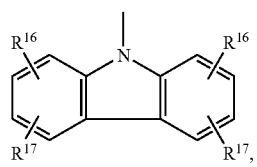

wherein $R^{15}$, $R^{16}$ and $R^{17}$ independently from each other stands for hydrogen, $C_1$-$C_8$-alkyl or $C_1$-$C_8$-alkoxy, $R^{5'}$ and $R^{6''}$ independently from each other stands for hydrogen, $C_1$-$C_8$-alkyl or $C_1$-$C_8$-alkoxy, and $X^1$ stands for hydrogen, or $C_1$-$C_8$-alkyl, are preferred as guest compounds.

Particularly preferred guest choromophores of DPP compounds represented by the formula I and IV are the following compounds:

| Compound (of formula IV) | $A^9 = A^{10}$ | $R^{13} = R^{14}$ |
|---|---|---|
| G-1 | Me | —$CH_3$ |
| G-2 | " | n-$C_4H_9$ |
| G-3 | " | n-$CH_{12}H_{25}$ |
| G-4 | | ethyl-3,5-dimethylphenyl |
| G-5 | | n-$C_4H_9$ |
| G-6 | | $C_2H_5$ |
| G-7 | | n-$C_6H_{13}$ |
| G-8 | | n-$C_6H_{13}$ |
| G-9 | | n-$C_6H_{13}$ |

| Compound (of formula I) | $A^1 = A^2$ | $R^1 = R^2$ |
|---|---|---|
| G-10 | | n-$C_4H_9$ |
| G-11 | | n-$C_{12}H_{25}$ |
| G-12 | " | n-$C_4H_9$ |
| G-13 | Me | $CH_3$ |

-continued
| | | |
|---|---|---|
| G-14 | 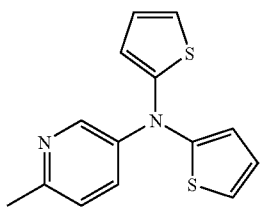 | CH₃ |
| G-15 | " | n-C₄H₉ |
| G-16 | 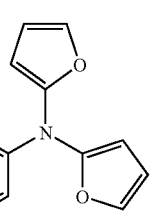 | n-C₄H₉ |
| G-17 | 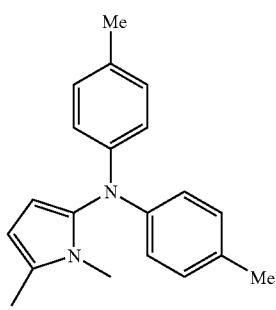 | n-C₄H₉ |
| G-18 | 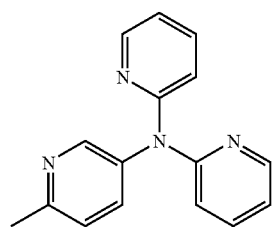 | n-C₄H₉ |
| G-19 | 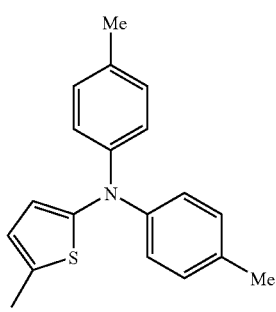 | CH₃ |
| G-20 | 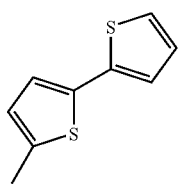 | n-C₄H₉ |
-continued
| | | |
|---|---|---|
| G-21 | 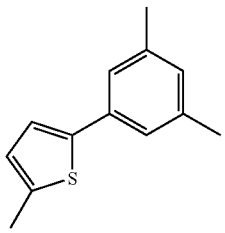 | n-C₄H₉ |
| G-22 | 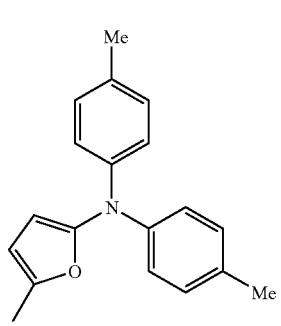 | n-C₄H₉ |
| G-23 | " | CH₃ |
| G-24 | 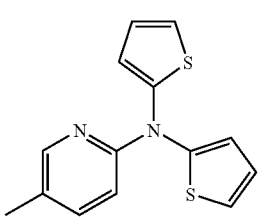 | n-C₄H₉ |
| G-25 | 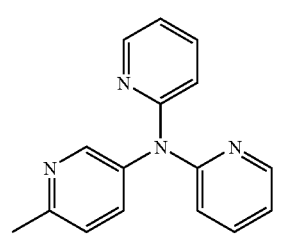 | n-C₄H₉ |
| G-26 | " | —CH(CH₃)₂ |
| G-27 | | CH₃ |
| G-28 | | CH₃ |

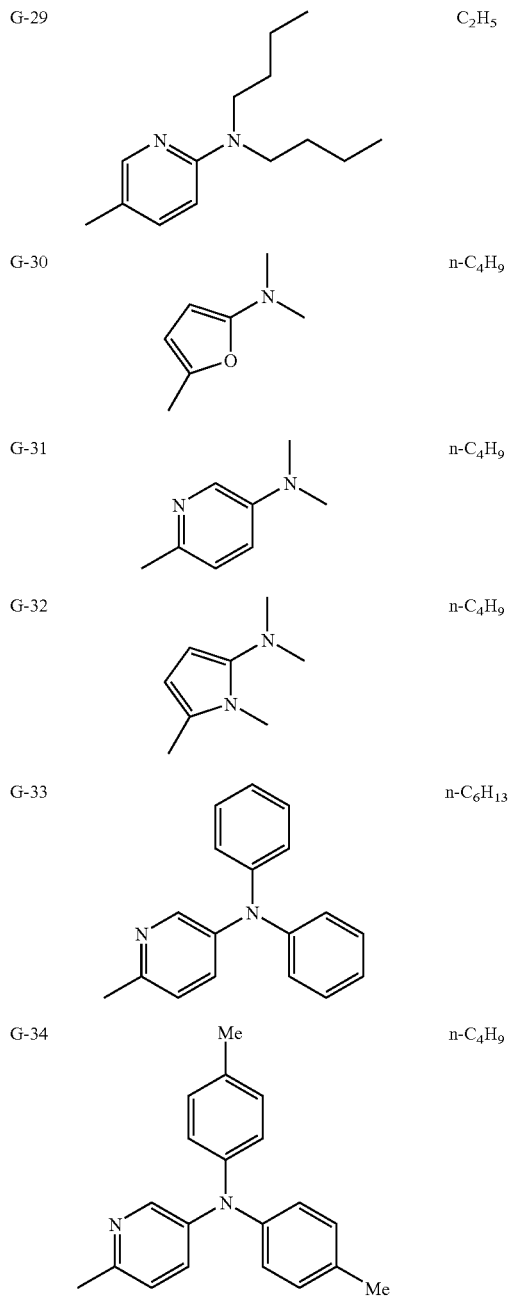

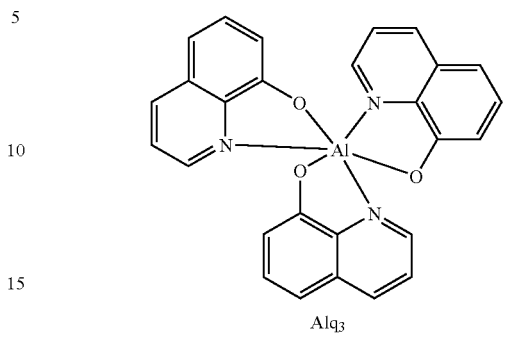

In addition, the compounds of formula I can be used with other known fluorescent compounds as host or guest compounds, for example, fused derivatives of aromatic hydrocarbons such as rubrene and perylene; fused heterocyclics such as pyridinothiadiasole, pyrazolopyridine and naphtalimide derivatives; rare rare earth complex as Eu, Ir, or Pt complex; zincporphyrin, rhodamine, deazafivain derivatives, coumarine derivatives, phenoxazones, quinacridones, dicyanoethenylarenes, $Alq_3$ and the derivatives thereof or the pyrromethene metal complexes disclosed in EP-A-1,253,151, JP2001 257077, JP2001 257078, and JP2001 297881.

Particularly preferred inventive host/guest compositions comprise compounds H-2 and G-12, H-17 and G-12, H-22 and G-12, H-12 and G-28, H-12 and G-30, H-2 and G-13, H-2 and G-33, H-4 and G-13, H-4 and G-33, $Alq_3$ and G-13 as well as $Alq_3$ and G-33.

A further embodiment of the present invention is directed to diketopyrrolopyrroles of formula

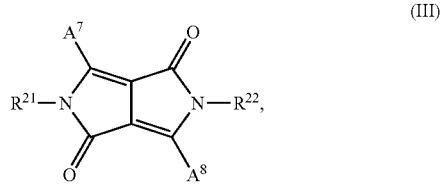

wherein $R^{21}$ and $R^{22}$ may be the same or different and are selected from a $C_1$-$C_{25}$alkyl group, an allyl group, which can be substituted one to three times with $C_1$-$C_4$alkyl, a cycloalkyl group, a cycloalkyl group, which can be condensed one or two times by phenyl which can be substituted one to three times with $C_1$-$C_4$-alkyl, halogen, nitro or cyano, an alkenyl group, a cycloalkenyl group, an alkynyl group, a haloalkyl group, a haloalkenyl group, a haloalkynyl group, a ketone or aldehyde group, an ester group, a carbamoyl group, a ketone group, a silyl group, a siloxanyl group, $A^3$ or —$CR^3R^4$—$(CH_2)_m$-$A^3$ wherein $R^3$ and $R^4$ independently from each other stand for hydrogen or $C_1$-$C_4$alkyl, or phenyl which can be substituted one to three times with $C_1$-$C_4$alkyl, $A^3$ stands for aryl or heteroaryl, in particular phenyl or 1- or 2-naphthyl which can be substituted one to three times with $C_1$-$C_8$alkyl and/or $C_1$-$C_8$alkoxy, and m stands for 0, 1, 2, 3 or 4, $A^7$ and $A^8$ independently from each other are selected from

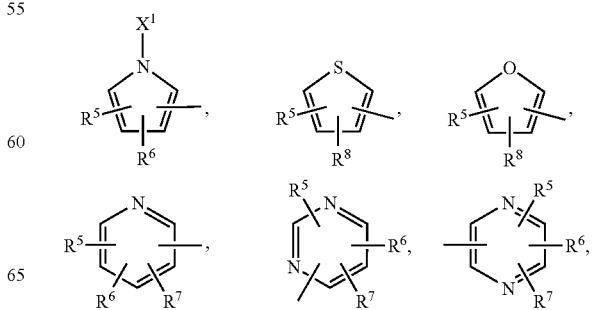

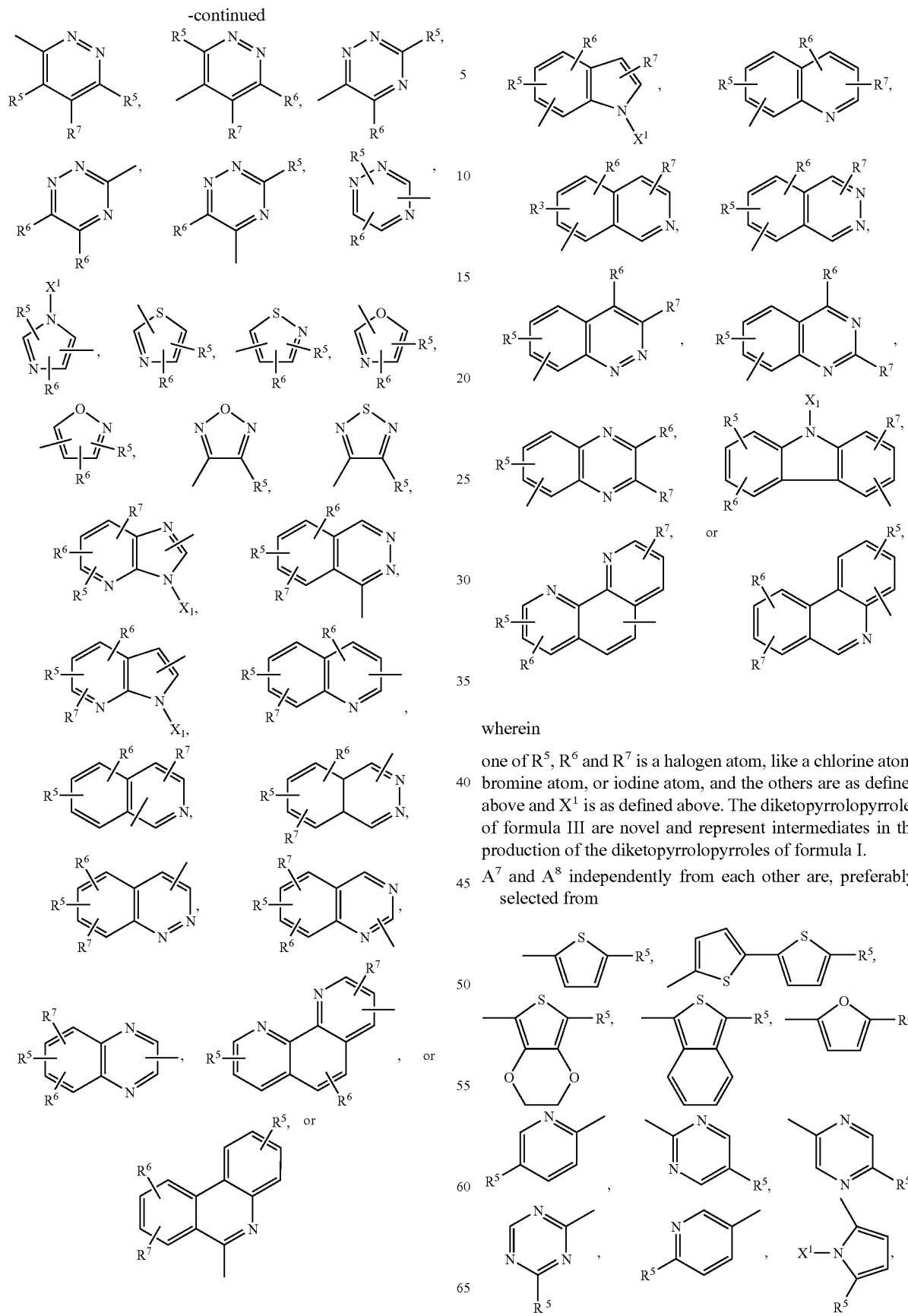

wherein
one of $R^5$, $R^6$ and $R^7$ is a halogen atom, like a chlorine atom, bromine atom, or iodine atom, and the others are as defined above and $X^1$ is as defined above. The diketopyrrolopyrroles of formula III are novel and represent intermediates in the production of the diketopyrrolopyrroles of formula I.

$A^7$ and $A^8$ independently from each other are, preferably, selected from $A^7$ and $A^8$ are independently of each other a group

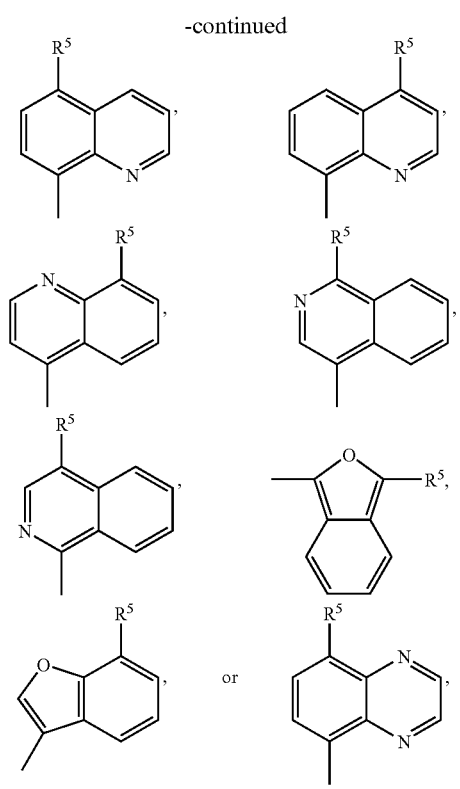

wherein R⁵ is a chlorine atom or a bromine atom.

The DPP compounds of formula II are described e.g. in U.S. Pat. No. 4,579,949, and/or can be prepared according to the method described therein (or in U.S. Pat. No. 4,659,775), in which an appropriate nitrile is reacted with a corresponding dialkyl or diaryl succinate, e.g. NC—Ar¹ and NC—Ar² are reacted with sodium tert.-amyl alcohol followed by the addition of diisopropyl succinate.

Compounds I are also available in analogy to the method described in EP-A-353,184, which comprises reacting a DPP compound of formula III with a nucleophilic agent such as a secondary amine, HNR¹²R¹³, preferably in a molar ratio of DPP III:nucleophilic agent in the range of 1.2:1 to 0.8:1, or, if R² has the same meaning as R¹ in the range of from 1:2.5 to 1:1, in the presence of an anhydrous dipolar aprotic solvent, and of an anhydrous base in an amount in the range of from usually 0.1 to 15 moles per mole of the nucleophilic agent, at a temperature in the range of from usually 100 to 220° C. and under a pressure generally in the range of from 100 to 300 kPa (for details see EP-A-1,087,005).

The DPP compounds of formula III are known and/or can be prepared e.g. according to the method described in EP-A-0353184.

The wording "at least two adjacent substituents form an aromatic or aliphatic fused ring system" means two adjacent substituents can form an aromatic ring, such as a phenyl or naphthyl ring, an aliphatic ring, such as a cyclohexyl ring, or a heterocyclic ring, such as a pyridine or pyrrole ring, wherein two or more of such rings can form a fused ring system with the group to which they are bonded.

The term "halogen" means fluorine, chlorine, bromine and iodine.

$C_1-C_{25}$alkyl is typically linear or branched—where possible—methyl, ethyl, n-propyl, isopropyl, n-butyl, sec.-butyl, isobutyl, tert.-butyl, n-pentyl, 2-pentyl, 3-pentyl, 2,2-dimethylpropyl, n-hexyl, n-heptyl, n-octyl, 1,1,3,3-tetramethylbutyl and 2-ethylhexyl, n-nonyl, decyl, undecyl, dodecyl, tetradecyl, pentadecyl, hexadecyl, heptadecyl, octadecyl, eicosyl, heneicosyl, docosyl, tetracosyl or pentacosyl, preferably $C_1-C_8$alkyl such as methyl, ethyl, n-propyl, isopropyl, n-butyl, sec.-butyl, isobutyl, tert.-butyl, n-pentyl, 2-pentyl, 3-pentyl, 2,2-dimethylpropyl, n-hexyl, n-heptyl, n-octyl, 1,1,3,3-tetramethylbutyl and 2-ethylhexyl, more preferably $C_1-C_4$alkyl such as typically methyl, ethyl, n-propyl, isopropyl, n-butyl, sec.-butyl, isobutyl, tert.-butyl.

The terms "haloalkyl, haloalkenyl and haloalkynyl" mean groups given by partially or wholly substituting the above-mentioned alkyl group, alkenyl group and alkynyl group with halogen, such as trifluoromethyl etc. The "aldehyde group, ketone group, ester group, carbamoyl group and amino group" include those substituted by an alkyl group, a cycloalkyl group, an aryl group, an aralkyl group or a heterocyclic group, wherein the alkyl group, the cycloalkyl group, the aryl group, the aralkyl group and the heterocyclic group may be unsubstituted or substituted. The term "silyl group" means a group of formula —SiR⁶²R⁶³R⁶⁴, wherein R⁶², R⁶³ and R⁶⁴ are independently of each other a $C_1-C_8$alkyl group, in particular a $C_1-C_4$ alkyl group, a $C_6-C_{24}$aryl group or a $C_7-C_{12}$aralkyl group, such as a trimethylsilyl group. The term "siloxanyl group" means a group of formula —O—SiR⁶²R⁶³R⁶⁴, wherein R⁶², R⁶³ and R⁶⁴ are as defined above, such as a trimethylsiloxanyl group.

Examples of $C_1-C_8$alkoxy are methoxy, ethoxy, n-propoxy, isopropoxy, n-butoxy, sec.-butoxy, isobutoxy, tert.-butoxy, n-pentoxy, 2-pentoxy, 3-pentoxy, 2,2-dimethylpropoxy, n-hexoxy, n-heptoxy, n-octoxy, 1,1,3,3-tetramethylbutoxy and 2-ethylhexoxy, preferably $C_1-C_4$alkoxy such as typically methoxy, ethoxy, n-propoxy, isopropoxy, n-butoxy, sec.-butoxy, isobutoxy, tert.-butoxy. The term "alkylthio group" means the same groups as the alkoxy groups, except that the oxygen atom of ether linkage is replaced by a sulfur atom.

The term "aryl group" is typically $C_6-C_{24}$aryl, such as phenyl, 1-naphthyl, 2-naphthyl, 4-biphenyl, phenanthryl, terphenyl, pyrenyl, 2- or 9-fluorenyl or anthracenyl, preferably $C_6-C_{12}$aryl such as phenyl, 1-naphthyl, 2-naphthyl, 4-biphenyl, which may be unsubstituted or substituted.

The term "aralkyl group" is typically $C_7-C_{24}$aralkyl, such as benzyl, 2-benzyl-2-propyl, β-phenyl-ethyl, α,α-dimethylbenzyl, ω-phenyl-butyl, ω,ω-dimethyl-ω-phenyl-butyl, ωphenyl-dodecyl, ω-phenyl-octadecyl, ω-phenyl-eicosyl or ω-phenyl-docosyl, preferably $C_7-C_{18}$aralkyl such as benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl or ω-phenyl-octadecyl, and particularly preferred $C_7-C_{12}$aralkyl such as benzyl, 2-benzyl-2-propyl, β-phenyl-ethyl, α,α-dimethylbenzyl, ω-phenyl-butyl, or ω,ω-dimethyl-ω-phenyl-butyl, in which both the aliphatic hydrocarbon group and aromatic hydrocarbon group may be unsubstituted or substituted.

The term "aryl ether group" is typically a $C_{6-24}$aryloxy group, that is to say O—$C_{6-24}$aryl, such as, for example, phenoxy or 4-methoxyphenyl. The term "aryl thioether group" is typically a $C_{6-24}$arylthio group, that is to say S—$C_{6-24}$aryl, such as, for example, phenylthio or 4-methoxyphenylthio. The term "carbamoyl group" is typically a $C_{1-18}$carbamoyl radical, preferably $C_{1-8}$carbamoyl radical, which may be unsubstituted or substituted, such as, for example, carbamoyl, methylcarbamoyl, ethylcarbamoyl, n-butylcarbamoyl, tert-butylcarbamoyl, dimethylcarbamoyloxy, morpholinocarbamoyl or pyrrolidinocarbamoyl.

The term "cycloalkyl group" is typically $C_5$-$C_{12}$cycloalkyl, such as cyclopentyl, cyclohexyl, cycloheptyl, cyclooctyl, cyclononyl, cyclodecyl, cycloundecyl, cyclododecyl, preferably cyclopentyl, cyclohexyl, cycloheptyl, or cyclooctyl, which may be unsubstituted or substituted. The term "cycloalkenyl group" means an unsaturated alicyclic hydrocarbon group containing one or more double bonds, such as cyclopentenyl, cyclopentadienyl, cyclohexenyl and the like, which may be unsubstituted or substituted. The cycloalkyl group, in particular a cyclohexyl group, can be condensed one or two times by phenyl which can be substituted one to three times with $C_1$-$C_4$-alkyl, halogen and cyano. Examples of such condensed cyclohexyl groups are:

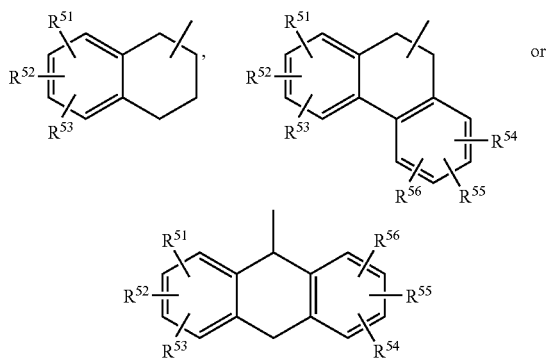

in particular

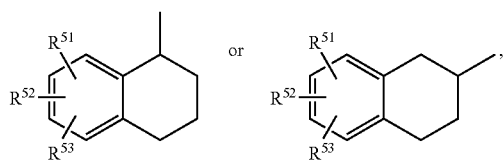

wherein $R^{51}$, $R^{52}$, $R^{53}$, $R^{54}$, $R^{55}$ and $R^{56}$ are independently of each other $C_1$-$C_8$-alkyl, $C_1$-$C_8$-alkoxy, halogen and cyano, in particular hydrogen.

The wording "a group comprising a five-membered heterocyclic ring, containing one to three heteroatoms selected from the group of nitrogen, oxygen and sulfur" means a single five-membered heterocyclic ring, such as thienyl, furyl, furfuryl, 2H-pyranyl, pyrrolyl, imidazolyl, or pyrazolyl, or a five-membered heterocyclic ring which is part of a fused ring system, which is formed by the five-membered heterocyclic ring with aryl, heteroaryl and/or cycloalkyl groups, which can optionally be substituted. Examples of such groups are contained in the list of groups for $A^1$ and $A^2$ as well as in the definition of heteroaryl or heterocyclic groups.

The wording "a group comprising a six-membered heterocyclic ring, containing one to three heteroatoms selected from the group of nitrogen, oxygen and sulfur" means a single six-membered heterocyclic ring, such as pyridyl, triazinyl, pyrimidinyl, pyrazinyl, pyridazinyl, or a six-membered heterocyclic ring which is part of a fused ring system, which is formed by the six-membered heterocyclic ring with aryl, heteroaryl and/or cycloalkyl groups, which can optionally be substituted. Examples of such groups are contained in the list of groups for $A^1$ and $A^2$ as well as in the definition of heteroaryl or heterocyclic group.

The term "heteroaryl or heterocyclic group" is a ring with five to seven ring atoms, wherein nitrogen, oxygen or sulfur are the possible hetero atoms, and is typically an unsaturated heterocyclic radical with five to 18 atoms having at least six conjugated π-electrons such as thienyl, benzo[b]thienyl, dibenzo[b,d]thienyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, carbolinyl, benzotriazolyl, benzoxazolyl, phenanthridinyl, acridinyl, perimidinyl, phenanthrolinyl, phenazinyl, isothiazolyl, phenothiazinyl, isoxazolyl, furazanyl or phenoxazinyl, preferably the above-mentioned mono- or bicyclic heterocyclic radicals.

The terms "aryl" and "alkyl" in alkylamino groups, dialkylamino groups, alkylarylamino groups, arylamino groups and diarylgroups are typically $C_1$-$C_{25}$alkyl and $C_6$-$C_{24}$aryl, respectively.

The above-mentioned groups can be substituted by a $C_1$-$C_8$alkyl, a hydroxyl group, a mercapto group, $C_1$-$C_8$alkoxy, $C_1$-$C_8$alkylthio, halogen, halo-$C_1$-$C_8$alkyl, a cyano group, an aldehyde group, a ketone group, a carboxyl group, an ester group, a carbamoyl group, an amino group, a nitro group, a silyl group or a siloxanyl group.

The present invention relates further to an electroluminescent device having the fluorescent diketopyrrolopyrroles of formula I or the compositions according to the present invention between an anode and a cathode and emitting light by the action of electrical energy.

Typical constitutions of latest organic electroluminescent devices are:

(i) an anode/a hole transporting layer/an electron transporting layer/a cathode, in which the compounds or compositions of the present invention are used either as positive-hole transport compound or composition, which is exploited to form the light emitting and hole transporting layers, or as electron transport compounds or compositions, which can be exploited to form the light-emitting and electron transporting layers, (ii) an anode/a hole transporting layer/a light-emitting layer/ an electron transporting layer/a cathode, in which the compounds or compositions form the light-emitting layer regardless of whether they exhibit positive-hole or electron transport properties in this constitution, (iii) an anode/a hole injection layer/a hole transporting layer/a light-emitting layer/an electron transporting layer/a cathode, (iv) an anode/a hole transporting layer/a light-emitting layer/a positive hole inhibiting layer/an electron transporting layer/a cathode, (v) an anode/a hole injection layer/a hole transporting layer/a light-emitting layer/a positive hole inhibiting layer/an electron transporting layer/a cathode, (vi) an anode/a light-emitting layer/an electron transporting layer/a cathode, (vii) an anode/a light-emitting layer/a positive hole inhibiting layer/an electron transporting layer/a cathode, (viii) a mono-layer containing a light emitting material alone or a combination a light emitting material and any of materials of the hole transporting layer, the hole-blocking layer and/or the electron transporting layer, and (ix) a multi-layered structure described in (ii) to (vii), wherein a light emitting layer is the monolayer defined in (viii).

The compounds and compositions of the present invention can, in principal be used for any organic layer, such as, for example, hole transporting layer, light emitting layer, or electron transporting layer, but are preferably used as the light emitting material in the light emitting layer.

Thin film type electroluminescent devices usually consist essentially of a pair of electrodes and at least one charge transporting layer in between. Usually two charge transporting layers, a hole transporting layer (next to the anode) and an electron transporting layer (next to the cathode) are present. Either one of them contains—depending on its properties as hole-transporting or electron-transporting material—an inorganic or organic fluorescence substance as light-emitting material. It is also common, that a light-emitting material is used as an additional layer between the hole-transporting and the electron-transporting layer. In the above mentioned device structure, a hole injection layer can be constructed between an anode and a hole transporting layer and/or a positive hole inhibiting layer can be constructed between a light emitting layer and an electron transporting layer to maximise hole and electron population in the light emitting layer, reaching large efficiency In charge recombination and intensive light emission.

The devices can be prepared in several ways. Usually, vacuum evaporation is used for the preparation. Preferably, the organic layers are laminated in the above order on a commercially available indium-tin-oxide ("ITO") glass substrate held at room temperature, which works as the anode in the above constitutions. The membrane thickness is preferably in the range of 1 to 10,000 nm, more preferably 1 to 5,000 nm, more preferably 1 to 1,000 nm, more preferably 1 to 500 nm. The cathode metal, such as a Mg/Ag alloy, a binary Li—Al or LiF—Al system with an thickness In the range of 50-200 nm is laminated on the top of the organic layers. The vacuum during the deposition is preferably less than 0.1333 Pa ($1\times10^{-3}$ Torr), more preferably less than $1.333\times10^{-3}$ Pa ($1\times10^{-5}$ Torr), more preferably less than $1.333\times10^{-4}$ Pa ($1\times10^{-6}$ Torr).

As anode usual anode materials which possess high work function such as metals like gold, silver, copper, aluminum, indium, iron, zinc, tin, chromium, titanium, vanadium, cobalt, nickel, lead, manganese, tungsten and the like, metallic alloys such as magnesium/copper, magnesium/silver, magnesium/aluminum, aluminum/indium and the like, semiconductors such as Si, Ge, GaAs and the like, metallic oxides such as indium-tin-oxide ("ITO"), ZnO and the like, metallic compounds such as CuI and the like, and furthermore, electroconducting polymers such polyacetylene, polyaniline, polythiophene, polypyrrole, polyparaphenylene and the like, preferably ITO, most preferably ITO on glass as substrate can be used.

Of these electrode materials, metals, metallic alloys, metallic oxides and metallic compounds can be transformed into electrodes, for example, by means of the sputtering method. In the case of using a metal or a metallic alloy as a material for an electrode, the electrode can be formed also by the vacuum deposition method. In the case of using a metal or a metallic alloy as a material forming an electrode, the electrode can be formed, furthermore, by the chemical plating method (see for example, Handbook of Electrochemistry, pp 383-387, Mazuren, 1985). In the case of using an electroconducting polymer, an electrode can be made by forming it into a film by means of anodic oxidation polymerization method onto a substrate which is previously provided with an electroconducting coating. The thickness of an electrode to be formed on a substrate is not limited to a particular value, but, when the substrate is used as a light emitting plane, the thickness of the electrode is preferably within the range of from 1 nm to 300 nm, more preferably, within the range of from 5 to 200 nm so as to ensure transparency.

In a preferred embodiment ITO is used on a substrate having an ITO film thickness in the range of from 10 nm (100 Å) to 1μ (10000 Å), preferably from 20 nm (200 Å) to 500 nm (5000 Å). Generally, the sheet resistance of the ITO film is chosen in the range of not more than 100 Ω/cm², preferably not more than 50 Ω/cm².

Such anodes are commercially available from Japanese manufacturers, such as Geomatech Co. Ltd., Sanyo Vacuum Co. Ltd., Nippon Sheet Glass Co. Ltd.

As substrate either an electronconducting or electrically insulating material can be used. In case of using an electroconducting substrate, a light emitting layer or a positive hole transporting layer is directly formed thereupon, while in case of using an electrically insulating substrate, an electrode is firstly formed thereupon and then a light emitting layer or a positive hole transporting layer is superposed.

The substrate may be either transparent, semi-transparent or opaque. However, in case of using a substrate as an indicating plane, the substrate must be transparent or semi-transparent.

Transparent electrically insulating substrates are, for example, inorganic compounds such as glass, quartz and the like, organic polymeric compounds such as polyethylene, polypropylene, polymethylmethacrylate, polyacrylonitrile, polyester, polycarbonate, polyvinylchloride, polyvinylalcohol, polyvinylacetate and the like. Each of these substrates can be transformed into a transparent electroconducting substrate by providing it with an electrode according to one of the methods described above.

Examples of semitransparent electrically insulating substrates are inorganic compounds such as alumina, YSZ (yttrium stabilized zirconia) and the like, organic polymeric compounds such as polyethylene, polypropylene, polystyrene, epoxy resins and the like. Each of these substrates can be transformed into a semitransparent electroconducting substrate by providing it with an electrode according to one of the abovementioned methods.

Examples of opaque electroconducting substrates are metals such as aluminum, indium, iron, nickel, zinc, tin, chromium, titanium, copper, silver, gold, platinum and the like, various eletroplated metals, metallic alloys such as bronze, stainless steel and the like, semiconductors such as Si, Ge, GaAs, and the like, electroconducting polymers such as polyaniline, polythiophene, polypyrrole, polyacetylene, polyparaphenylene and the like.

A substrate can be obtained by forming one of the above listed substrate materials to a desired dimension. It is preferred that the substrate has a smooth surface. Even, if it has a rough surface, it will not cause any problem for practical use, provided that it has round unevenness having a curvature of not less than 20 μm. As for the thickness of the substrate, there is no restriction as far as it ensures sufficient mechanical strength.

As cathode usual cathode materials which possess low work function such as alkali metals, earth alkaline metals, group 13 elements, silver, and copper as well as alloys or mixtures thereof such as sodium, lithium, potassium, calcium, lithium fluoride (LiF), sodium-potassium alloy, magnesium, magnesium-silver alloy, magnesium-copper alloy, magnesium-aluminum alloy, magnesium-indium alloy, aluminum, aluminum-aluminum oxide alloy, aluminum-lithium alloy, indium, calcium, and materials exemplified in EP-A 499,011 such as electroconducting polymers e.g. polypyrrole, polythiophene, polyaniline, polyacetylene etc., preferably Mg/Ag alloys, LiF—Al or Li—Al compositions can be used.

In a preferred embodiment a magnesium-silver alloy or a mixture of magnesium and silver, or a lithium-aluminum alloy, lithium fluoride-aluminum alloy or a mixture of lithium and aluminum can be used in a film thickness in the range of from 10 nm (100 Å) to 1 μm (10000 Å), preferably from 20 nm (200 Å) to 500 nm (5000 Å).

Such cathodes can be deposited on the foregoing electron transporting layer by known vacuum deposition techniques described above.

In a preferred ambodiment of this invention a light-emitting layer can be used between the hole transporting layer and the electron transporting layer. Usually the light-emitting layer is prepared by forming a thin film on the hole transporting layer.

As methods for forming said thin film, there are, for example, the vacuum deposition method, the spin-coating method, the casting method, the Langmuir-Blodgett ("LB") method and the like. Among these methods, the vacuum deposition method, the spin-coating method and the casting method are particularly preferred in view of ease of operation and cost.

In case of forming a thin film using a composition by means of the vacuum deposition method, the conditions under which the vacuum deposition is carried out are usually strongly dependent on the properties, shape and crystalline state of the compound(s). However, optimum conditions are usually as follows: temperature of the heating boat: 100 to 400° C.; substrate temperature: −100 to 350° C.; pressure: $1.33 \times 10^4$ Pa ($1 \times 10^2$ Torr) to $1.33 \times 10^{-4}$ Pa ($1 \times 10^{-6}$ Torr) and deposition rate: 1 pm to 6 nm/sec.

In an organic EL element, the thickness of the light emitting layer is one of the factors determining its light emission properties. For example, if a light emitting layer is not sufficiently thick, a short circuit can occur quite easily between two electrodes sandwiching said light emitting layer, and therefor, no EL emission is obtained. On the other hand, if the light emitting layer is excessively thick, a large potential drop occurs inside the light emitting layer because of its high electrical resistance, so that the threshold voltage for EL emission increases. Accordingly, the thickness of the organic light emitting layer is limited to the range of from 5 nm to 5 μm, preferably to the range of from 10 nm to 500 nm.

In the case of forming a right emitting layer by using the spin-coating method and the casting method, ink jet printing method, the coating can be carried out using a solution prepared by dissolving the composition in a concentration of from 0.0001 to 90% by weight in an appropriate organic solvent such as benzene, toluene, xylene, tetrahydrofurane, methyltetrahydrofurane, N,N-dimethylformamide, dichloromethane, dimethylsulfoxide and the like. If the concentration exceeds 90% by weight, the solution usually is so viscous that it no longer permits forming a smooth and homogenous film. On the other hand, if the concentration is less than 0.0001% by weight, the efficiency of forming a film is too law to be economical. Accordingly, a preferred concentration of the composition is within the range of from 0.01 to 80% by weight.

In the case of using the above spin-coating or casting method, it is possible to further improve the homogeneity and mechanical strength of the resulting layer by adding a polymer binder to the solution for forming the light emitting layer. In principle, any polymer binder may be used, provided that it is soluble in the solvent in which the composition is dissolved. Examples of such polymer binders are polycarbonate, polyvinylalcohol, polymethacrylate, polymethylmethacrylate, polyester, polyvinylacetate, epoxy resin and the like. However, if the solid content composed of the polymer binder and the composition exceeds 99% by weight, the fluidity of the solution is usually so low that it is impossible to form a light emitting layer excellent in homogeneity. On the other hand, if the content of the composition is substantially smaller than that of the polymer binder, the electrical resistance of said layer is very large, so that it does not emit light unless a high voltage is applied thereto. Accordingly, the preferred ratio of the polymer binder to the composition is chosen within the range of from 10:1 to 1:50 by weight, and the solid content composed of both components in the solution is preferably within the range of from 0.01 to 80% by weight, and more preferably, within the range of 0.1 to 60% by weight.

As hole-transporting layers known organic hole transporting compounds such as polyvinyl carbazole

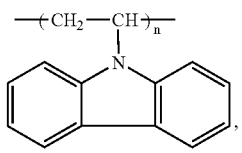

a TPD compound disclosed in J. Amer. Chem. Soc. 90 (1968) 3925:

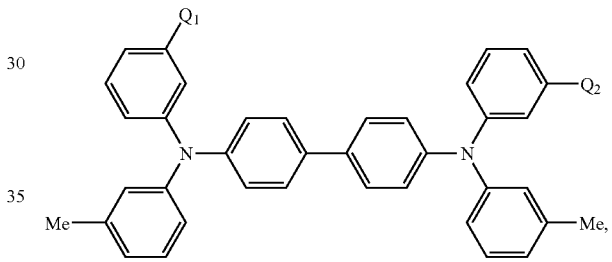

wherein $Q_1$ and $Q_2$ each represent a hydrogen atom or a methyl group;

a compound disclosed in J. Appl. Phys. 65(9) (1989) 3610:

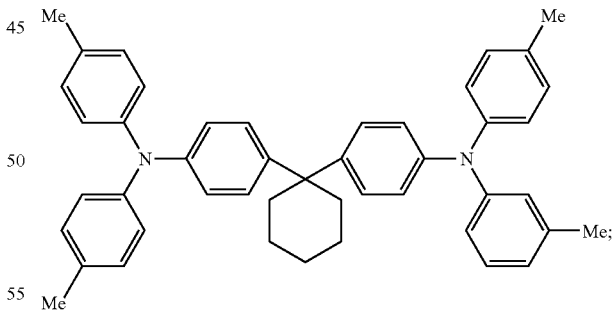

a stilbene based compound

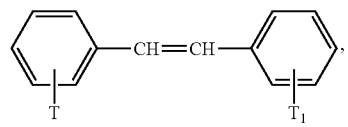

wherein T and $T_1$ stand for an organic radical;

a hydrazone based compound

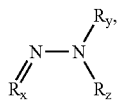

wherein Rx, Ry and Rz stand for an organic radical, and the like can be used.

Compounds to be used as a positive hole transporting material are not restricted to the above listed compounds. Any compound having a property of transporting positive holes can be used as a positive hole transporting material such as triazole derivatives, oxadiazole derivatives, imidazole derivatives, polyarylalkane derivatives, pyrazoline derivative, pyrazolone derivatives, phenylene diamine derivatives, arylamine derivatives, amino substituted chalcone derivatives, oxazole derivatives, stilbenylanthracene derivatives, fluorenone derivatives, hydrazone derivatives, stilbene derivatives, copolymers of aniline derivatives, PEDOT (poly(3,4-ethylenedioxy-thiophene)) and the derivatives thereof, electroconductive oligomers, particularly thiophene oligomers, porphyrin compounds, aromatic tertiary amine compounds, stilbenyl amine compounds etc.

Particularly, aromatic tertiary amine compounds such as N,N,N',N'-tetraphenyl-4,4'-diaminobiphenyl, N,N'-diphenyl-N,N'-bis(3-methylphenyl)-4,4'-diaminobiphenyl (TPD), 2,2'-bis(di-p-torylaminophenyl)propane, 1,1'-bis(4-di-torylaminophenyl)-4phenylcyclohexane, bis(4-dimethylamino-2-methylphenyl)phenylmethane, bis(4-di-p-tolylaminophenyl)phenylmethane, N,N'-diphenyl-N,N'-di(4-methoxyphenyl)-4,4'-diaminobiphenyl, N,N,N',N'-tetraphenyl-4,4'-diaminodiphenylether, 4,4'-bis(diphenylamino)quaterphenyl, N,N,N-tri(p-tolyl)amine, 4-(di-p-tolylamino)-4'-[4-(di-p-tolylamino)stilyl]stilbene, 4-N,N-diphenylamino-(2-diphenylvinyl)benzene, 3-methoxy-4'-N,N-diphenylaminostilbene, N-phenylcarbazole etc. are used.

Furthermore, 4,4'-bis[N-(1-naphtyl)-N-phenylamino]biphenyl disclosed in U.S. Pat. No. 5,061,569 and the compounds disclosed in EP-A 508,562, in which three triphenylamine units are bound to a nitrogen atom, such as 4,4',4"-tris[N-(3-methylphenyl)-N-phenylamino]triphenylamine, can be used.

A positive hole transporting layer can be formed by preparing an organic film containing at least one positive hole transporting material on the anode. The positive hole transporting layer can be formed by the vacuum deposition method, the spin-coating method, the casting method, ink jet printing method, the LB method and the like. Of these methods, the vacuum deposition method, the spin-coating method and the casting method are particularly preferred in view of ease and cost.

In the case of using the vacuum deposition method, the conditions for deposition may be chosen in the same manner as described for the formation of a light emitting layer (see above). If it is desired to form a positive hole transporting layer comprising more than one positive hole transporting material, the coevaporation method can be employed using the desired compounds.

In the case of forming a positive hole transporting layer by the spin-coating method or the casting method, the layer can be formed under the conditions described for the formation of the light emitting layer (see above).

As in the case of forming the light emitting layer a smoother and more homogeneous positive hole transporting layer can be formed by using a solution containing a binder and at least one positive hole transporting material. The coating using such a solution can be performed in the same manner as described for the light emitting layer. Any polymer binder may be used, provided that it is soluble in the solvent in which the at least one positive hole transporting material is dissolved. Examples of appropriate polymer binders and of appropriate and preferred concentrations are given above when describing the formation of a light emitting layer.

The thickness of the positive hole transporting layer is preferably chosen in the range of from 0.5 to 1000 nm, preferably from 1 to 100 nm, more preferably from 2 to 50 nm.

As hole injection materials known organic hole transporting compounds such as metal-free phthalocyanine ($H_2Pc$), copper-phthalocyanine (Cu-Pc) and their derivatives as described, for example, in JP64-7635 can be used. Furthermore, some of the aromatic amines defined as hole transporting materials above, which have a lower ionisation potential than the hole transporting layer, can be used.

A hole injection layer can be formed by preparing an organic film containing at least one hole injection material between the anode layer and the hole transporting layer. The hole injection layer can be formed by the vacuum deposition method, the spin-coating method, the casting method, the LB method and the like. The thickness of the layer is preferably from 5 nm to 5 μm, and more preferably from 10 nm to 100 nm.

The electron transporting materials should have a high electron injection efficiency (from the cathode) and a high electron mobility. The following materials can be exemplified for electron transporting materials: tris(8-hydroxyquinolinato)-aluminum(III) and its derivatives, bis(10-hydroxybenzo[h]quinolinolato)beryllium(II) and its derivatives, oxadiazole derivatives, such as 2-(4-biphenyl)-5-(4-tert.-butylphenyl)-1,3,4-oxadiazole and its dimer systems, such as 1,3-bis(4-tert.-butylphenyl-1,3,4)oxadiazolyl)biphenylene and 1,3-bis(4-tert.-butylphenyl-1,3,4-oxadiazolyl)phenylene, dioxazole derivatives, triazole derivatives, coumarine derivatives, imidazopyridine derivatives, phenanthroline derivatives or perylene tetracarboxylic acid derivatives disclosed in Appl. Phys. Lett. 48 (2) (1986) 183.

An electron transporting layer can be formed by preparing an organic film containing at least one electron transporting material on the hole transporting layer or on the light-emitting layer. The electron transporting layer can be formed by the vacuum deposition method, the spin-coating method, the casting method, the LB method and the like.

It is preferred that the positive hole inhibiting materials for a positive hole inhibiting layer have high electron injection/transporting efficiency from the electron transporting layer to the light emission layer and also have higher ionisation potential than the light emitting layer to prevent the flowing out of positive holes from the light emitting layer to avoid a drop in luminescence efficiency.

As the positive hole inhibiting material known materials, such as Balq, TAZ and phenanthroline derivatives, e.g. bathocuproine (BCP), can be used:

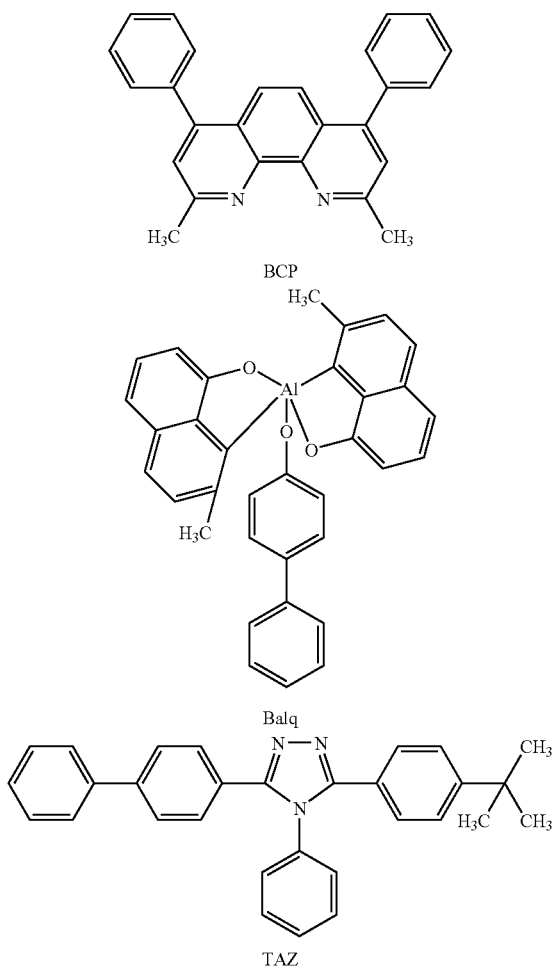

BCP

Balq

TAZ

The positive hole inhibiting layer can be formed by preparing an organic film containing at least one positive hole inhibiting material between the electron transporting layer and the light-emitting layer. The positive hole inhibiting layer can be formed by the vacuum deposition method, the spin-coating method, the casting method, ink jet printing method, the LB method and the like. The thickness of the layer preferably is chosen within the range of from 5 nm to 2 μm, and more preferably, within the range of from 10 nm to 100 nm.

As in the case of forming a light emitting layer or a positive hole transporting layer, a smoother and more homogeneous electron transporting layer can be formed by using a solution containing a binder and at least one electron transporting material.

The thickness of an electron transporting layer is preferably chosen in the range of from 0.5 to 1000 nm, preferably from 1 to 100 nm, more preferably from 2 to 50 nm.

In general, the host chromphore is a diketopyrrolopyrrole having a photoluminescence emission peak at 500 to 720 nm, preferably 520 to 630 nm, most preferred 540 to 600 nm. The host chromphore is preferably a diketopyrrolopynrole of formula II.

The light-emitting compositions have a fluorescence emission maximum in the range of from 500 to 780, preferably from 520 to 750, more preferred from 540 to 700 nm. Further, the inventive compounds preferably exhibit an absorption maximum in the range of 450 to 600 nm.

The light-emitting compositions usually exhibit a fluorescence quantum yield ("FQY") in the range of from 1>FQY≧0.3 (measured in aerated toluene or DMF). Further, in general, the inventive compositions exhibit a molar absorption coefficient In the range of from 5000 to 100000.

Another embodiment of the present invention relates to a method of coloring high molecular weight organic materials (having a molecular weight usually in the range of from $10^3$ to $10^7$ g/mol; comprising biopolymers, and plastic materials, including fibres) by incorporating therein the inventive compounds or compositions by methods known in the art.

The inventive compounds and compositions can be used, as described for the DPP compounds of formula I' In EP-A-1087005, for the preparation of inks, for printing inks in printing processes, for flexographic printing, screen printing, packaging printing, security ink printing, intaglio printing or offset printing, for pre-press stages and for textile printing, for office, home applications or graphics applications, such as for paper goods, for example, for ballpoint pens, felt tips, fiber tips, card, wood, (wood) stains, metal, inking pads or inks for impact printing processes (with impact-pressure ink ribbons), for the preparation of colorants, for coating materials, for industrial or commercial use, for textile decoration and industrial marking, for roller coatings or powder coatings or for automotive finishes, for high-solids (low-solvent), water-containing or metallic coating materials or for pigmented formulations for aqueous paints, for the preparation of pigmented plastics for coatings, fibers, platters or mold carriers, for the preparation of non-impact-printing material for digital printing, for the thermal wax transfer printing process, the ink jet printing process or for the thermal transfer printing process, and also for the preparation of color filters, especially for visible light in the range from 400 to 700 nm, for liquid-crystal displays (LCDs) or charge combined devices (CCDs) or for the preparation of cosmetics or for the preparation of polymeric ink particles, toners, dye lasers, dry copy toners liquid copy toners, or electrophotographic toners, and electroluminescent devices.

Another preferred embodiment concerns the use of the inventive compounds and compositions for color changing media. There are three major techniques in order to realize full-color organic electroluminescent devices:

(i) use of the three primary colors blue, green and red generated by electroluminescence, (ii) conversion of the electroluminescent blue or white to photoluminescent green and red via color changing media (CCM), which absorb the above electroluminescent blue, and fluorescence in green and red.

(iii) conversion of the white luminescent emission to blue, green and red via color filters.

The inventive compounds or compositions are useful for EL materials for the above category (i) and, in addition, for the above mention technique (ii). This is because the invented compounds or compositions can exhibit strong photoluminescence as well as electroluminescence.

Technique (ii) is, for example, known from U.S. Pat. No. 5,126,214, wherein EL blue with a maximum wavelength of ca. 470-480 nm is converted to green and red using coumarin, 4-(dicyanomethylene)-2-methyl-6-(p-dimethylaminostyryl)-4H-pyran, pyridine, rhodamine 6G, phenoxazone or other dyes.

The inventive compounds or compositions are useful for EL materials for the above category (iii) as an element of white luminescent in combination of other compensatory electroluminescence to construct white luminescent. This is because compounds or compositions can exhibit strong photoluminescence as well as electrolunimescence.

Illustrative examples of suitable organic materials of high molecular weight which can be colored with the inventive compositions are described in EP-A-1087005.

Particularly preferred high molecular weight organic materials, in particular for the preparation of a paint system, a printing ink or ink, are, for example, cellulose ethers and esters, e.g. ethylcellulose, nitrocellulose, cellulose acetate and cellulose butyrate, natural resins or synthetic resins (polymerization or condensation resins) such as aminoplasts, in particular urea/formaldehyde and melamine/formaldehyde resins, alkyd resins, phenolic plastics, polycarbonates, polyolefins, polystyrene, polyvinyl chloride, polyamides, polyurethanes, polyester, ABS, ASA, polyphenylene oxides, vulcanized rubber, casein, silicone and silicone resins as well as their possible mixtures with one another.

It is also possible to use high molecular weight organic materials in dissolved form as film formers, for example boiled linseed oil, nitrocellulose, alkyd resins, phenolic resins, melamine/formaldehyde and urea/formaldehyde resins as well as acrylic resins.

Said high molecular weight organic materials may be obtained singly or in admixture, for example in the form of granules, plastic materials, melts or in the form of solutions, in particular for the preparation of spinning solutions, paint systems, coating materials, inks or printing inks.

In a particularly preferred embodiment of this invention, the inventive compounds and compositions are used for the mass coloration of polyvinyl chloride, polyamides and, especially, polyolefins such as polyethylene and polypropylene as well as for the preparation of paint systems, including powder coatings, inks, printing inks, color filters and coating colors.

Illustrative examples of preferred binders for paint systems are alkyd/melamine resin paints, acryl/melamine resin paints, cellulose acetate/cellulose butyrate paints and two-pack system lacquers based on acrylic resins which are crosslinkable with polyisocyanate.

Hence, another embodiment of the present invention relates to a composition comprising (a) 0.01 to 50, preferably 0.01 to 5, particularly preferred 0.01 to 2% by weight, based on the total weight of the coloured high molecular organic material, of a fluorescent diketopyrrolopyrrole according to formula I or of a composition according to the present invention, and (b) 99.99 to 50, preferably 99.99 to 95, particularly preferred 99.99 to 98% by weight, based on the total weight of the coloured high molecular organic material, of a high molecular organic material, and (c) optionally, customary additives such as rheology improvers, dispersants, fillers, paint auxiliaries, siccatives, plasticizers, UV-stabilizers, and/or additional pigments or corresponding precursors in effective amounts, such as e.g. from 0 to 50% by weight, based on the total weight of (a) and (b).

To obtain different shades, the inventive fluorescent DPP compounds of formula I or the inventive compositions may advantageously be used in admixture with fillers, transparent and opaque white, colored and/or black pigments as well as customary luster pigments in the desired amount.

For the preparation of paints systems, coating materials, color filters, inks and printing inks, the corresponding high molecular weight organic materials, such as binders, synthetic resin dispersions etc. and the inventive compounds or compositions are usually dispersed or dissolved together, if desired together with customary additives such as dispersants, fillers, paint auxiliaries, siccatives, plasticizers and/or additional pigments or pigment precursors, in a common solvent or mixture of solvents. This can be achieved by dispersing or dissolving the individual components by themselves, or also several components together, and only then bringing all components together, or by adding everything together at once.

Hence, a further embodiment of the present invention relates to a method of using the inventive compounds or compositions for the preparation of dispersions and the corresponding dispersions, and paint systems, coating materials, color filters, inks and printing inks comprising the inventive compositions.

A particularly preferred embodiment relates to the use of the inventive compounds or compositions for the preparation of fluorescent tracers for e.g. leak detection of fluids such as lubricants, cooling systems etc., as well as to fluorescent tracers or lubricants comprising the inventive compositions.

For the pigmentation of high molecular weight organic material, the inventive compounds or compositions, optionally in the form of masterbatches, are mixed with the high molecular weight organic materials using roll mills, mixing apparatus or grinding apparatus. Generally, the pigmented material is subsequently brought into the desired final form by conventional processes, such as calandering, compression molding, extrusion, spreading, casting or injection molding.

For pigmenting lacquers, coating materials and printing inks the high molecular weight organic materials and the inventive compounds or compositions, alone or together with additives, such as fillers, other pigments, siccatives or plasticizers, are generally dissolved or dispersed in a common organic solvent or solvent mixture. In this case it is possible to adopt a procedure whereby the individual components are dispersed or dissolved individually or else two or more are dispersed or dissolved together and only then are all of the components combined.

The present invention additionally relates to inks comprising a coloristically effective amount of the pigment dispersion of the inventive compositions.

The weight ratio of the pigment dispersion to the ink in general is chosen in the range of from 0.001 to 75% by weight, preferably from 0.01 to 50% by weight, based on the overall weight of the ink.

The preparation and use of color filters or color-pigmented high molecular weight organic materials are well-known in the art and described e.g. in Displays 14/2, 1151 (1993), EP-A 784085, or GBA 2,310,072.

The color filters can be coated for example using inks, especially printing inks, which can comprise pigment dispersions comprising the inventive compositions or can be prepared, for example, by mixing a pigment dispersion comprising an inventive composition with chemically, thermally or photolytically structurable high molecular weight organic material (so-called resist). The subsequent preparation can be carried out, for example, in analogy to EP-A 654 711 by application to a substrate, such as a LCD (liquid crystal display), subsequent photostructuring and development.

Particular preference for the production of color filters is given to pigment dispersions comprising an inventive compound or composition which possess non-aqueous solvents or dispersion media for polymers.

The present invention relates, moreover, to toners comprising a pigment dispersion containing an inventive compound or composition or a high molecular weight organic material pigmented with an inventive composition in a coloristically effective amount. The present invention additionally relates to colorants, colored plastics, polymeric ink particles, or non-impact-printing material comprising an inventive composition, preferably in the form of a dispersion, or a high molecular weight organic material pigmented with an inventive composition in a coloristically effective amount.

A coloristically effective amount of the pigment dispersion according to this invention comprising an inventive composition denotes in general from 0.0001 to 99.99% by weight, preferably from 0.001 to 50% by weight and, with particular preference, from 0.01 to 50% by weight, based on the overall weight of the material pigmented therewith.

The inventive compositions can be applied to colour polyamides, because they do not decompose during the incorporation into the polyamides. Further, they exhibit an exceptionally good lightfastness, a superior heat stability, especially in plastics.

The organic EL device of the present invention has significant industrial values since it can be adapted for a flat panel display of an on-wall television set, a flat light-emitting device, a light source for a copying machine or a printer, a light source for a liquid crystal display or counter, a display signboard and a signal light. The compounds and compositions of the present invention can be used in the fields of an organic EL device, an electrophotographic photoreceptor, a photoelectric converter, a solar cell, an image sensor, and the like.

The following examples are for illustrative purposes only and are not to be construed to limit the scope of the instant invention in any manner whatsoever. In the examples the "parts" denote "parts by weight" and the "percentages" denote "percentages by weight", unless otherwise stated.

EXAMPLE 1

3.8 g of sodium and 300 ml of tert-amyl alcohol are heated up to 100° C. under a nitrogen atmosphere and stirred for 15 hours. The reaction mixture is allowed to cool to room temperature. 27.7 g of 2-cyano-5-bromopyridine are added and heated up to 110° C. As soon as the temperature has been reached, a solution of 16.2 g of diisopropyl succinate and 100 ml of tert-amyl alcohol is added over 1 hour using a dropping funnel. When the addition has been completed, the reaction mixture is kept for 20 hours at 100° C. and cooled down to 65° C. Then 300 ml of water are added and the resultant pigment suspension is filtered at room temperature, washed with methanol and water until washings run colorless and dried at 100° C. in vacuum, affording 6.6 g (9.8% of theory, based on dibutyl succinate) of 1,4-diketo-3,6-bis-2-(5-bromopyridin-yl)-pyrrolo-(3,4-c)-pyrrole.

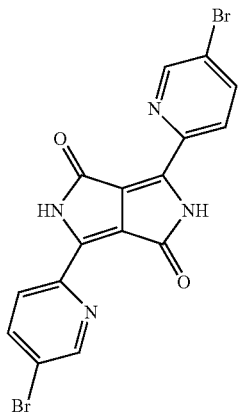

A-1

2.0 g of 1,4-diketo-3,6-bis-2-(5-bromopyridine-yl)-pyrrolo-(3,4-c)-pyrrole are slurred in 1-methyl 2-pyrrolidinone for 2 hours at room temperature. 1.5 g of potassium tert-butoxide are added to the slurry under nitrogen. After stirred for 3 hours, 2.4 g of n-butyl iodide are added to the reaction mixture and agitated additional 18 hours. Then, the mixture is poured into 50 ml of water and the precipitate is collected by filtration and purified by column chromatography (silica gel, dichloromethane as eluant), followed by washing with methanol.

After drying 450 mg of 2,5,-dibutyl-1,4,-diketo-3,6-bis-2-(5-bromopyridine-yl)pyrrolo(3,4,-c) pyrrole are obtained (yield 18%).

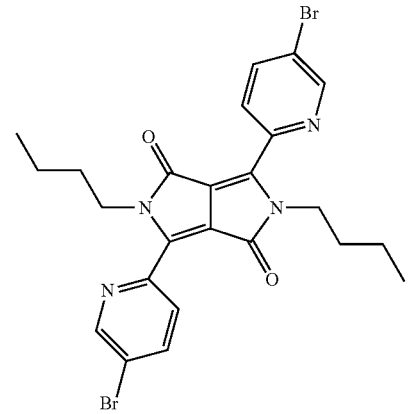

A-2

EXAMPLE 2

200 mg of 2,5-di-butyl-1,4,-diketo-3,6-bis-2-(5-bromopyridine-yl)pyrrolo(3,4,-c) pyrrole, 151 mg of diphenylamine, 6 mg of palladium(II)acetate, 20 mg of bis-diphenylphosphino ferrocene, 233 mg of cesium carbonate and 50 ml of dry xylene are placed in a three necked flask and stirred at 150° C. under nitrogen for 7 hours. After the completion of the reaction, xylene is removed under reduced pressure and the residue is purified by column chromatography (silica gel, dichloromethane as eluant) After drying, 0.12 g (46%) of the desired product are obtained as red solid.

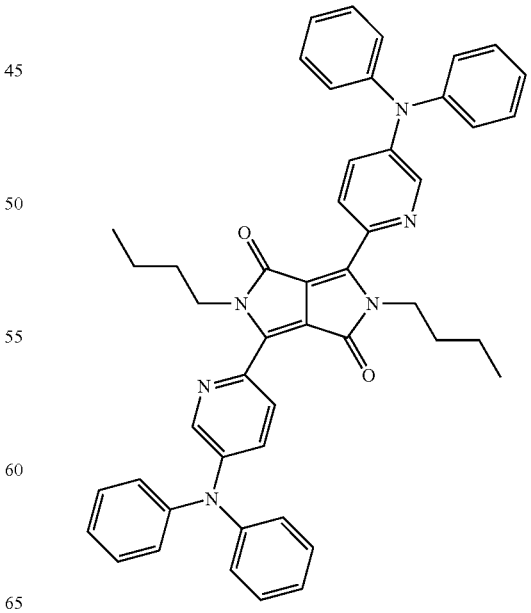

G-12

EXAMPLE 3

Example 1 is repeated except that methyl iodide is used in place of butyl iodide. A red solid (yield: 18%) is obtained.

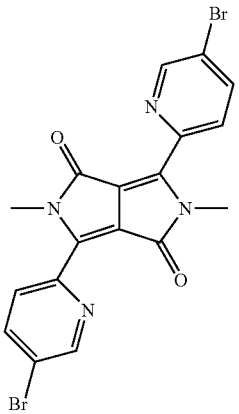

A-3

EXAMPLE 4

220 mg of 2,5-dimethyl-1,4-diketo-3,6-bis-2-(5-bromopyridin-yl) pyrrolo(3,4,-c) pyrrole, 228 mg of ditolylamine, 6 mg of palladium(II)acetate, 20 mg of bis-diphenylphosphino ferrocene, 300 mg of cesium carbonate and 10 ml of dry xylene are placed in a three necked flask and stirred at 150° C. under nitrogen for 4 hours. After completion of the reaction, xylene is removed under reduced pressure and the residue is purified by column chromatography (silica gel, dichloromethane as eluant) After drying, 0.08 g (24%) of the desired product are obtained as red solid.

G-13

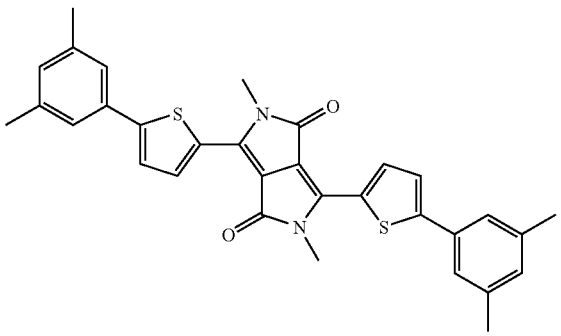

EXAMPLE 5

6.01 g of sodium and 400 ml of tert-amyl alcohol are heated up to 100° C. under a nitrogen atmosphere and stirred for 18 hours. The reaction mixture is allowed to cool to room temperature, 44.66 g of 2-cyano-5-bromothiophene are added and heated up to 110° C. As soon as the temperature has been reached, a solution of 24.3 g of diisopropyl succinate and 100 ml of tert-amyl alcohol is added over 5 hours using a dropping funnel. When the addition has been completed, the reaction mixture is kept for 20 hours at 120° C. and cooled down to 65° C. Then 300 ml of water and 20 ml of acetic acid are added and the resultant pigment suspension is filtered at room temperature, washed with methanol and water until washings run colorless, and dried, affording 8.0 g 7.3% of theory, based on dibutyl succinate) of 1,4-diketo-3,6-bis-2-(5-bromothiophene-yl)-pyrrolo-(3,4-c)-pyrrole.

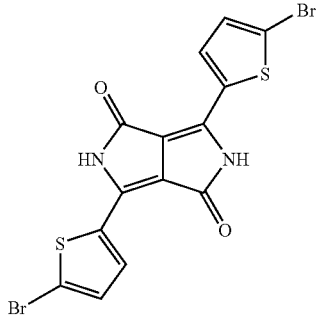

A-4

Example 3 is repeated, except using A-4 in place of A-1, whereby a red solid is obtained (yield: 5%).

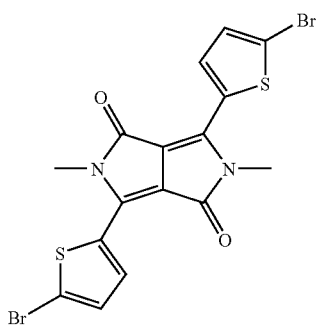

A-5

EXAMPLE 6

200 mg of A-5, 150 mg of 3,5-dimethylphenylboronic acid, 10 mg of tetrakis-(triphenylphosphino)palladium, 166 mg of potassium carbonate and 10 ml of dry xylene are placed in a three-necked flask and stirred at 130° C. for 1 hour. The xylene is removed and the resultant product is purified by column chromatography (silica gel, dichroromethane as eluant). After drying, 0.02 g of the desired product (A-8) are obtained as purple solid.

A-6

EXAMPLE 7

Example 5 is repeated, except using 2-cyano-3,4-ethylene-dioxythiophene in place of 2-cyano-5-bromothiophene, whereby a dark purple solid is obtained (yield: 15%).

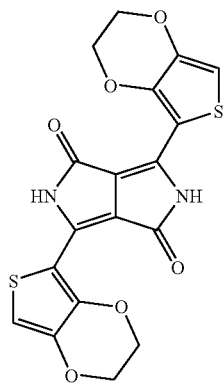

A-7

Example 3 is repeated, except that A-7 is used in place of A-3, whereby a red solid is obtained (yield: 25%).

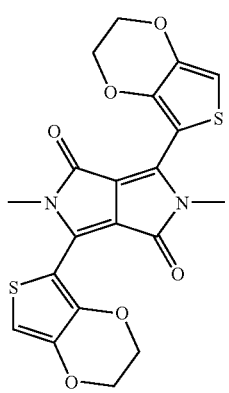

A-8

EXAMPLE 8

Example 4 is repeated, except that A-5 is used in place of A-3, whereby a red purple solid is obtained (yield: 10%).

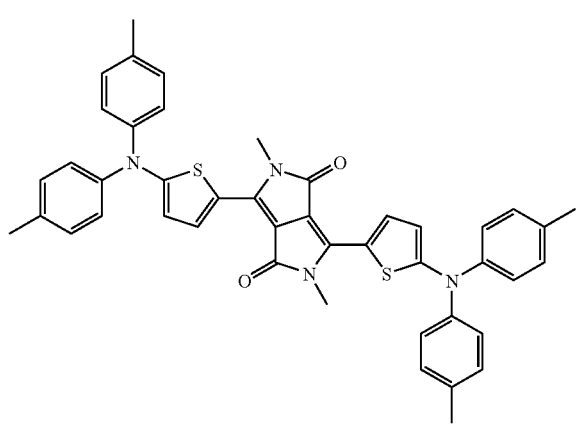

A-9

EXAMPLE 9

Example 1 is repeated except that n-dodecyl iodide is used in place of butyl iodide. A red solid (yield: 13%) is obtained.

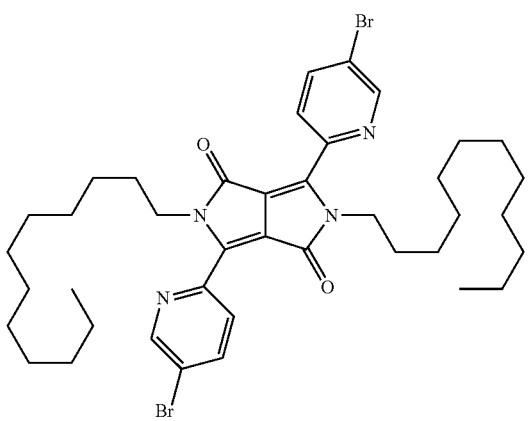

A-10

EXAMPLE 10

Example 4 is repeated, except that A-10 and diphenylamine are used in place of A-3 and ditolylamine, respectively, whereby a purple solid is obtained (yield: 21%).

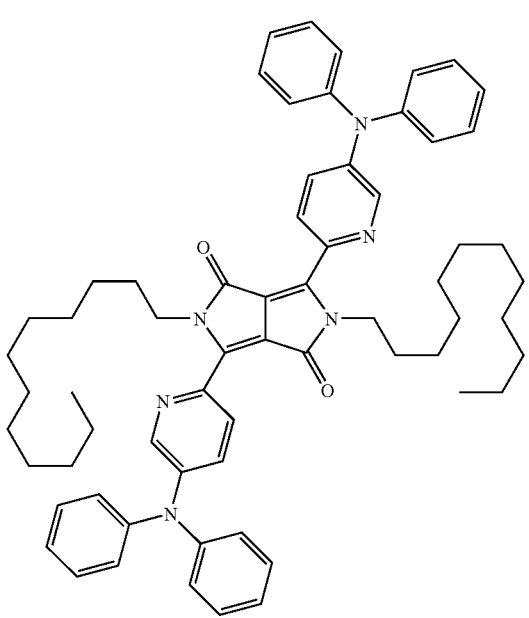

G-11

EXAMPLE 11

Example 1 is repeated, except that 2-cyanopyridine is used in place of 2-cyano-5-bromopyridine, whereby a red solid is obtained (yield: 32%).

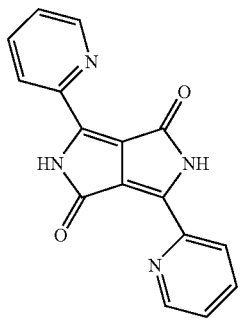

A-11

Example 3 is repeated, except that A-11 is used in place of A-1 whereby a red solid is obtained (yield: 69%).

TABLE 1

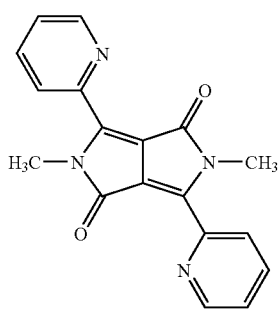

A-12

| | | Physical properties | | |
|---|---|---|---|---|
| Example No. | Compound | Absorption[1] Peak (nm) | PL[2] Peak (nm) | Mp.[3] [° C.] |
| 1 | A-1 | 523, 8330[4] | 545 | 300< |
| 1 | A-2 | 546, 21942 | 575 | 231-233 |
| 2 | G-12 | 586, 61662 | 606 | 295-301 |
| 3 | A-3 | 543, 5079 | 572 | >300 |
| 4 | G-13 | 585, 74649 | 613 | >300 |
| 5 | A-4 | — | — | >300 |
| 6 | A-5 | 570, 49003 | 588, 631 | >300 |
| 7 | A-6 | 602, 19655 | 624 | >300 |
| 8 | A-7 | 544, 26802[4] | 552 | >300 |
| 9 | A-8 | 511, 12283 | 564 | 292-295 |
| 10 | A-9 | 614, 61308 | 651 | 131-139 |
| 11 | A-10 | 547, 13654 | 577 | 151-153 |
| 12 | G-11 | 584, 54820 | 609 | 169-170 |
| 13 | A-11 | 511, 16685[4] | 530 | >300 |
| 14 | A-12 | 529, 12174 | 558 | 298-300 |

[1]In toluene;
[2]photoluminescence in toluene;
[3]melting point;
[4]in DMF.

APPLICATION EXAMPLE 1

Luminescent Element 1

A glass substrate (manufactured by Geomatek Co., a product prepared by electron beam vapor deposition method) on which an ITO transparent electroconductive film has been deposited up to a thickness of ca. 120 nm is cut into a size of 30×40 mm, and etched. The substrate thus obtained is subjected to ultrasonic washing with Semikoklin® 56 for 15 minutes, and then washed with hot ultra-pure water. Subsequently, the substrate is subjected to ultrasonic washing with acetone for 15 minutes, and then dried. Just before forming the substrate into an element, the substrate thus obtained is subjected to an air plasma treatment for half an hour and placed in a vacuum vapor deposition apparatus. The apparatus is evacuated until the inner pressure reached $1 \times 10^{-5}$ Pa or less. Then, according to the resistance heating method, a phthalocyanine copper complex (CuPc) is vapor-deposited up to a thickness of 20 nm to form a positive hole injection layer. N,N'-Di(naphthalen-1-y)-N,N'-diphenyl-benzidine (α-NPD) is vapor-deposited up to a thickness of 40 nm, to form a positive hole transporting layer. Subsequently, the DPP compound H-2 as host and the DPP compound G-13 (obtained in example 4) are co-deposited up to a thickness of 30 nm as guest as a light emitting layer, wherein the ratio of the DPP compounds is controlled by the deposition rate (H-2: G-13=100:1-0.5), to form a uniform light emitting layer. Subsequently, an $Alq_3$ layer having a thickness of 30 nm is vapor-deposited to form an electron transporting layer. Lithium fluoride (LiF) of thickness of 0.5 nm is vapor-deposited as electron injection material. On top of the electron injection material, aluminium (Al of a thickness of 150 nm is vapor-deposited to form a cathode, and an element having a size of 2×2 mm square is prepared.

The luminescent peak wavelength and emission intensity of the luminescent element 1 thus obtained is summarized in Table 1.

Application Example 1 is repeated to prepare luminescent elements 2 to 4. The light emitting materials used are specified in table 2 below.

TABLE 2

| | Light Emitting Material | | EL properties | |
|---|---|---|---|---|
| Luminescent Element | Host (99 wt %) | Guest (ca. 1 wt %) | Peak (nm) | Intensity (cd/m²) |
| 1 | H-2 | G-13 | 632 | 4308 |
| 2 | H-2 | G-12 | 624 | 16090 |
| 3 | H-17 | G-12 | 623 | 6929 |
| 4 | H-22 | G-12 | 616 | 16710 |
| Reference | Compound 1 (100 wt %)[1] | | 578 | 4386 |

[1]Compound 1 below (cf. example 81 in EP-A1087006) is used as light emitting material.

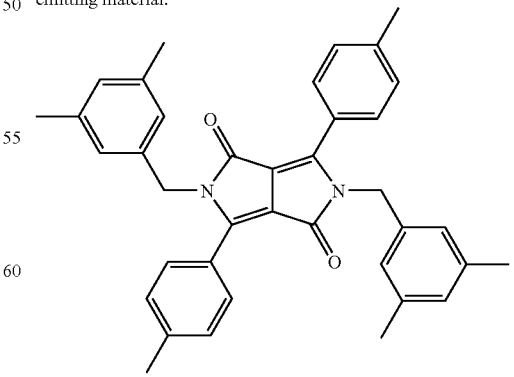

Compound 1

As evident from the EL properties of the luminescent elements the present invention can provide luminescent elements high in the efficiency of electrical energy utilisation and high in luminance.

EXAMPLE 12

The fluorescent dye A-12 and PMMA was dissolved in dichloromethane and a 3 mm diameter quarts rod is dipped into the solution, forming a thin film around the quarts rod. The sample is dried in a drying oven for 6 hours. The concentration of the A-12 in the PMMA film is 2 mM/l. The prepared quarts rod is used as a ring resonator and the light amplifier of the thin-film ring laser system.

The thin film ring laser is composed of two components. One is the quarts rod with a dye doped PMMA thin film, which works as a ring resonator. And the other is a planner waveguide made from a PMMA thin film. The pumping source is a third harmonic generation of a pulsed Nd:YAG laser; its wavelength is 355 nm and it's pulse width is 7 ns. When the pumping beam (083 mJ/cm$^2$) operates yellow laser oscillation with a centre wavelength of the laser at 530 nm is observed.

EXAMPLE 13

Example 1 was repeated except that n-hexyl iodide was used in place of butyl iodide (yield: 6%). Mp.=196-199° C.

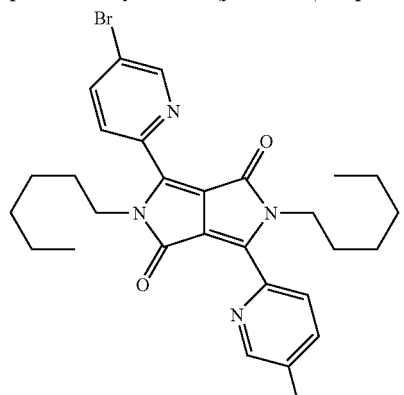

A-13

EXAMPLE 14

Example 4 was repeated except that A-13 was used in place of A-3 (yield: 45%). Mp.=268-270° C.

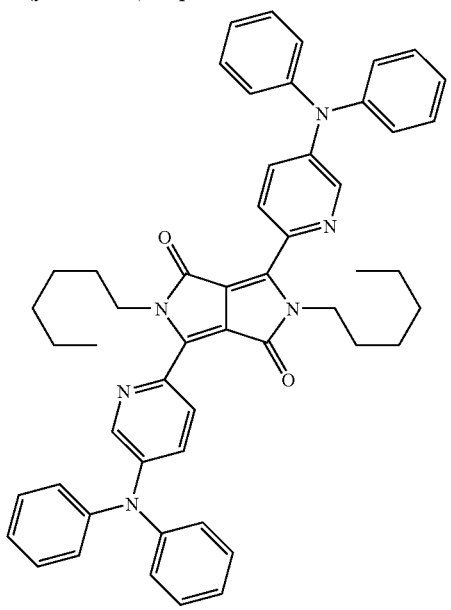

G-33

Luminescent Elements 5 and 6

Application Example 1 is repeated to prepare luminescent elements 5 and 6. The light emitting materials used are specified in table 3 below.

TABLE 3

| Luminescent Element | Light Emitting Material | | EL properties | |
|---|---|---|---|---|
| | Host (99 wt %) | Guest (ca. 1 wt %) | Peak (nm) | Intensity (cd/m$^2$) |
| 5 | H-2 | G-33 | 620 | 17405 |
| 6 | Alq$_3$ | G-33 | 626 | 5670 |

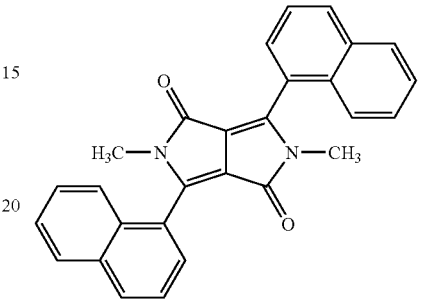

H-2

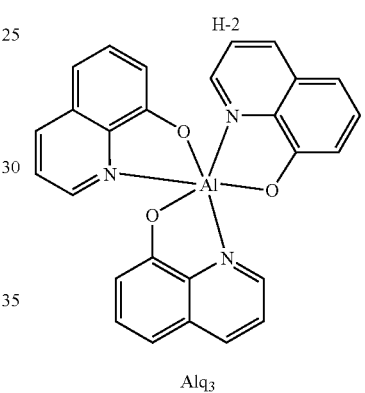

Alq$_3$

The invention claimed is:

1. A fluorescent diketopyrrolopyrrole of formula I

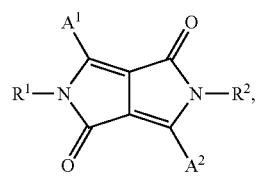

(I)

wherein

R$^1$ and R$^2$ may be the same or different and are a C$_1$-C$_{25}$alkyl group, which can be substituted by fluorine, chlorine or bromine, an allyl group, which can be substituted one to three times with C$_1$-C$_4$alkyl, C$_5$-C$_{12}$-cycloalkyl which can be substituted one to three times with C$_1$-C$_8$alkyl and/or C$_1$-C$_8$alkoxy, C$_5$-C$_{12}$cycloalkyl condensed one or two times by phenyl which can be substituted one to three times with C$_1$-C$_4$-alkyl, halogen, nitro or cyano, an alkenyl group, a cycloalkenyl group, an alkynyl group, a haloalkyl group, a haloalkenyl group, a haloalkynyl group, an aldehyde group, an ester group, a carbamoyl group, a ketone group, a silyl group, a siloxanyl group, A$^3$ or —CR$^3$R$^4$—(CH$_2$)$_m$-A$^3$ wherein R$^3$ and R$^4$ independently from each other stand for hydrogen or C$_1$-C$_4$alkyl, or phenyl which can be substituted one to three times with C$_1$-C$_4$alkyl, A³ stands for aryl or heteroaryl, which can be substituted one to three times with $C_1$-$C_8$alkyl and/or $C_1$-$C_8$alkoxy, and m stands for 0, 1, 2, 3 or 4, A¹ and A² are independently of each other a group

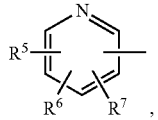

wherein $R^5$ is a group $NR^8R^9$, wherein $R^8$ is a hydrogen atom, an alkyl group, a cycloalkyl group, an aryl group, a heteroaryl group, a heterocyclic group, an aralkyl group, $R^9$ is an aryl group or a heteroaryl group, or $R^8$ and $R^9$ together with the nitrogen atom to which they are bonded form a five or six membered heterocyclic ring condensed by one or two optionally substituted phenyl groups, wherein $R^6$ and $R^7$ may be the same or different and are a hydrogen atom, a $C_1$-$C_{25}$alkyl group, a cycloalkyl group, an aralkyl group, an alkenyl group, a cycloalkenyl group, an alkynyl group, a hydroxyl group, a mercapto group, an alkoxy group, an alkylthio group, an aryl ether group, an aryl thioether group, an aryl group, a heterocyclic group, a halogen atom, a haloalkyl group, a haloalkenyl group, a haloalkynyl group, a cyano group, an aldehyde group, a carboxyl group, an ester group, a carbamoyl group, a nitro group, a silyl group, a siloxanyl group, a substituted or unsubstituted vinyl group, a group $NR^8R^9$, wherein $R^8$ and $R^9$ independently of each other stand for a hydrogen atom, an alkyl group, a cycloalkyl group, an aryl group, a heteroaryl group, a heterocyclic group, an aralkyl group, or $R^8$ and $R^9$ together with the nitrogen atom to which they are bonded form a five or six membered heterocyclic ring, which can be condensed by one or two optionally substituted phenyl groups.

2. A fluorescent diketopyrrolopyrrole according to claim 1, wherein $R^1$ and $R^2$ independently from each other are $C_1$-$C_8$alkyl, $C_5$-$C_{12}$-cycloalkyl, $C_5$-$C_{12}$-cycloalkyl substituted one to three times with $C_1$-$C_8$alkyl and/or $C_1$-$C_8$alkoxy, $C_5$-$C_{12}$cycloalkyl, condensed one or two times by phenyl which can be substituted one to three times with $C_1$-$C_4$-alkyl, halogen, nitro or cyano, phenyl or 1- or 2-naphthyl which can be substituted one to three times with $C_1$-$C_8$alkyl and/or $C_1$-$C_8$alkoxy, or —$CR^3R^4$—$(CH_2)_m$-$A^3$ wherein $R^3$ and $R^4$ stand for hydrogen, $A^3$ stands for phenyl or 1- or 2-naphthyl, which can be substituted one to three times with $C_1$-$C_8$alkyl and/or $C_1$-$C_8$alkoxy, and m stands for 0 or 1.

3. A fluorescent diketopyrrolopyrrole according to claim 1, wherein A¹ and A² are independently of each other

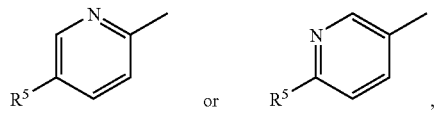

wherein $R^5$ is a group —$NR^8R^9$, wherein $R^8$ and $R^9$ independently from each other stand for

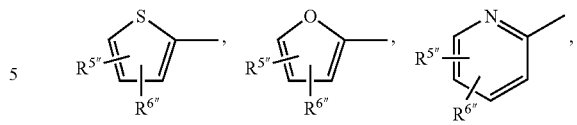

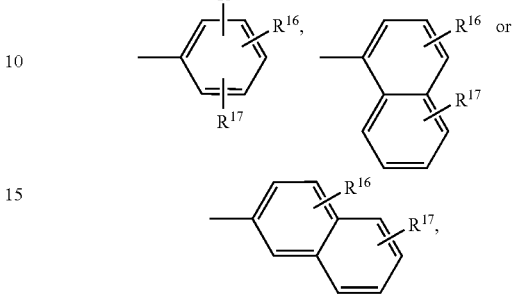

or $R^8$ and $R^9$ together with the nitrogen atom to which they are bonded form a five or six membered heterocyclic ring condensed by one or two optionally substituted phenyl groups, wherein $R^{15}$, $R^{16}$ and $R^{17}$ independently from each other stands for hydrogen, $C_1$-$C_8$-alkyl, $C_1$-$C_8$-alkoxy, or phenyl.

4. A fluorescent diketopyrrolopyrrole according to claim 3, which is

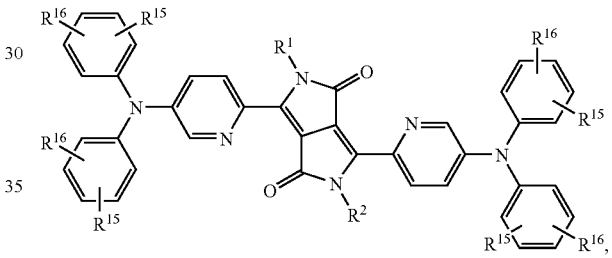

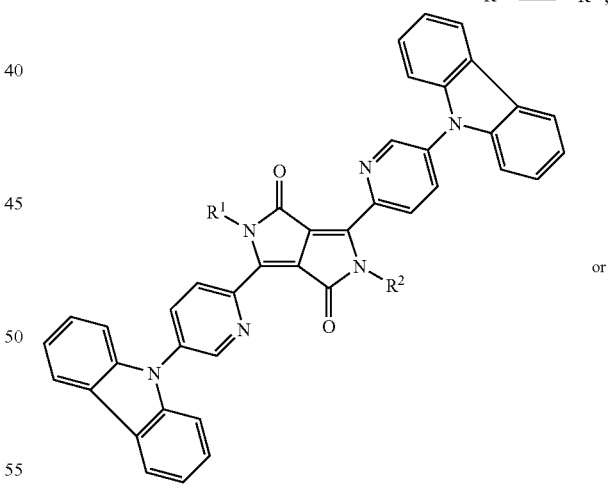

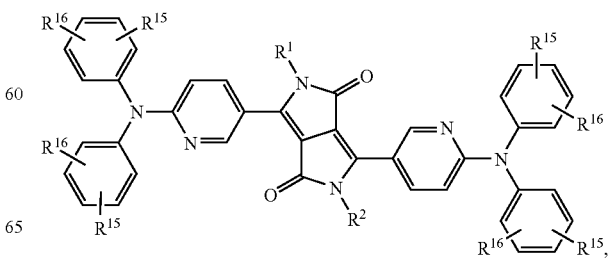

wherein

R[1] and R[2] are independently of each other a $C_1$-$C_{12}$alkyl group, a $C_5$-$C_7$cycloalkyl group, a $C_5$-$C_7$cycloalkyl group substituted one to three times with $C_1$-$C_8$alkyl and/or $C_1$-$C_8$alkoxy, or a $C_7$-$C_{14}$aralkyl group, which optionally can be substituted by one to three $C_1$-$C_8$-alkyl or $C_1$-$C_8$-alkoxy groups, and R[15] and R[16] stands for hydrogen, $C_1$-$C_8$-alkyl, $C_1$-$C_8$-alkoxy, or phenyl.

5. A fluorescent diketopyrrolopyrrole according to claim 4, which is

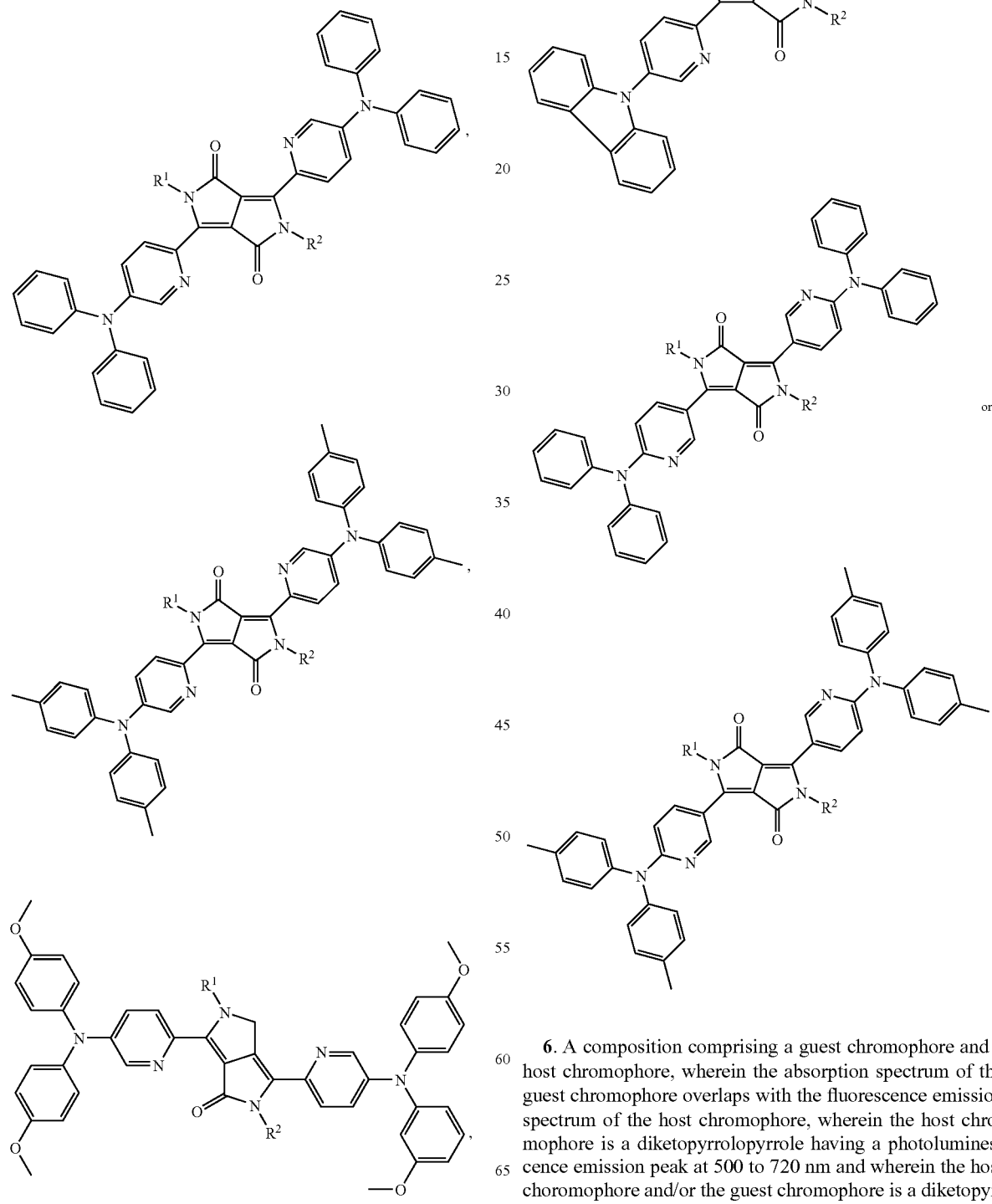

6. A composition comprising a guest chromophore and a host chromophore, wherein the absorption spectrum of the guest chromophore overlaps with the fluorescence emission spectrum of the host chromophore, wherein the host chromophore is a diketopyrrolopyrrole having a photoluminescence emission peak at 500 to 720 nm and wherein the host chromophore and/or the guest chromophore is a diketopyrrolopyrrole of formula I according to claim 1.

7. A composition comprising a guest chromophore and a host chromophore, wherein the absorption spectrum of the guest chromophore overlaps with the fluorescence emission spectrum of the host chromophore, wherein the host chromophore is a diketopyrrolopyrrole having a photoluminescence emission peak at 500 to 720 nm and wherein the the guest chromophore is a diketopyrrolopyrrole of formula I according to claim 1.

8. A composition comprising a guest chromophore and a host chromophore, wherein the absorption spectrum of the guest chromophore overlaps with the fluorescence emission spectrum of the host chromophore, wherein the host chromophore is a diketopyrrolopyrrole having a photoluminescence emission peak at 500 to 720 nm and wherein the guest chromophore is a diketopyrrolopyrrole of formula I according to claim 4.

9. A composition according to claim 7, wherein the host chromophore is a diketopyrrolopyrrole ("DPP") represented by formula II

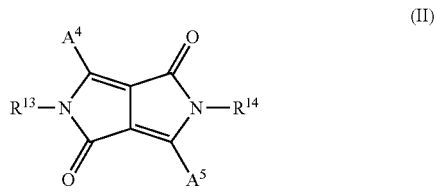

(II)

wherein $R^{13}$ and $R^{14}$ independently from each other stand for $C_1$-$C_{25}$-alkyl, which can be substituted by fluorine, chlorine or bromine, $C_5$-$C_{12}$-cycloalkyl or $C_5$-$C_{12}$-cycloalkyl, which can be condensed one or two times by phenyl which can be substituted one to three times with $C_1$-$C_4$-alkyl, halogen, nitro or cyano, silyl, $A^6$ or —$CR^{11}R^{12}$—$(CH_2)_m$-$A^6$, wherein $R^{11}$ and $R^{12}$ independently from each other stand for hydrogen, fluorine, chlorine, bromine, cyano or $C_1$-$C_4$alkyl, which can be substituted by fluorine, chlorine or bromine, or phenyl which can be substituted one to three times with $C_1$-$C_4$alkyl, $A^6$ stands for phenyl or 1- or 2-naphthyl which can be substituted one to three times with $C_1$-$C_8$alkyl, $C_1$-$C_8$alkoxy, halogen, nitro, cyano, phenyl, which can be substituted with $C_1$-$C_8$alkyl or $C_1$-$C_8$alkoxy one to three times, —$NR^{23}R^{24}$, wherein $R^{23}$ and $R^{24}$ represent hydrogen, $C_1$-$C_{25}$-alkyl, $C_5$-$C_{12}$-cycloalkyl or $C_6$-$C_{24}$-aryl, in particular phenyl or 1- or 2-naphthyl which can be substituted one to three times with $C_1$-$C_8$alkyl, $C_1$-$C_8$alkoxy, halogen or cyano, or phenyl, which can be substituted with $C_1$-$C_8$alkyl or $C_1$-$C_8$alkoxy one to three times, and m stands for 0, 1, 2, 3 or 4, $A^4$ and $A^5$ independently from each other stand for

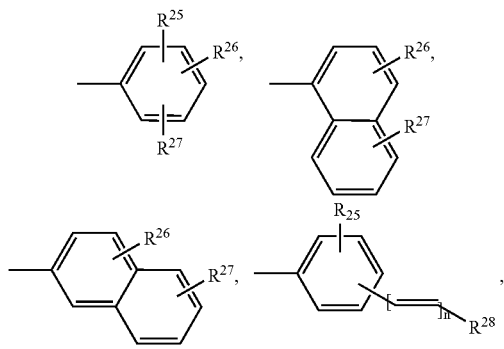

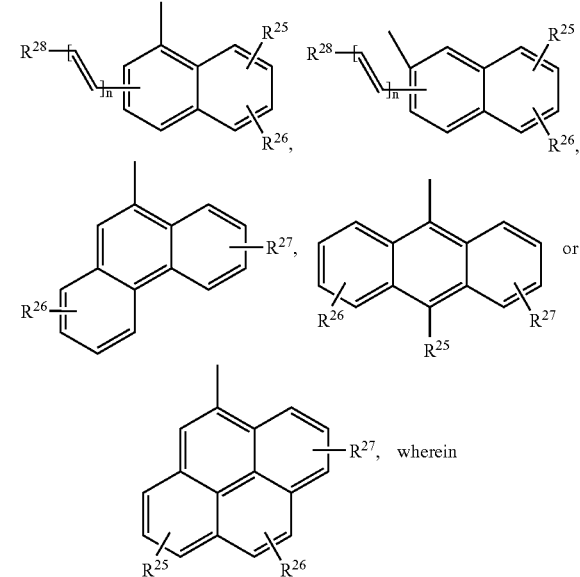

$R^{25}$, $R^{26}$, $R^{27}$ independently from each other stands for hydrogen, $C_1$-$C_{25}$alkyl, —$CR^{11}R^{12}$—$(CH_2)_m$-$A^6$, cyano, halogen, —$OR^{29}$, —$S(O)_pR^{30}$, or phenyl, which can be substituted one to three times with $C_1$-$C_8$alkyl or $C_1$-$C_8$alkoxy, wherein $R^{29}$ stands for $C_1$-$C_{25}$-alkyl, $C_5$-$C_{12}$-cycloalkyl, —$CR^{11}R^{12}$—$(CH_2)_m$-Ph, $C_6$-$C_{24}$-aryl, or a saturated or unsaturated heterocyclic radical comprising five to seven ring atoms, wherein the ring consists of carbon atoms and one to three hetero atoms selected from the group consisting of nitrogen, oxygen and sulfur, $R^{30}$ stands for $C_1$-$C_{25}$-alkyl, $C_5$-$C_{12}$-cycloalkyl, —$CR^{11}R^{12}$—$(CH_2)_m$-Ph, $R^{28}$ stands for $C_2$-$C_{20}$-heteroaryl or $C_6$-$C_{24}$-aryl, p stands for 0, 1, 2 or 3, m and n stands for 0, 1, 2, 3 or 4.

10. A composition according to claim 9, wherein the host chromophore is a diketopyrrolopyrrole represented by formula II wherein $R^{13}$ and $R^{14}$ independently from each other stand for $C_1$-$C_8$alkyl, $C_5$-$C_{12}$-cycloalkyl, which can be substituted one to three times with $C_1$-$C_8$alkyl and/or $C_1$-$C_8$alkoxy, phenyl or 1- or 2-naphthyl which can be substituted one to three times with $C_1$-$C_8$alkyl and/or $C_1$-$C_8$alkoxy, or —$CR^{11}R^{12}$—$(CH_2)_m$-$A^6$ wherein $R^{11}$ and $R^{12}$ stand for hydrogen, or $C_1$-$C_4$alkyl, $A^6$ stands for phenyl or 1- or 2-naphthyl, which can be substituted one to three times with $C_1$-$C_8$alkyl and/or $C_1$-$C_8$alkoxy, and m stands for 0 or 1.

11. A composition according to claim 10, wherein the host chromophore is a diketopyrrolopyrrole represented by formula II, wherein $A^4$ and $A^5$ independently from each other stand for

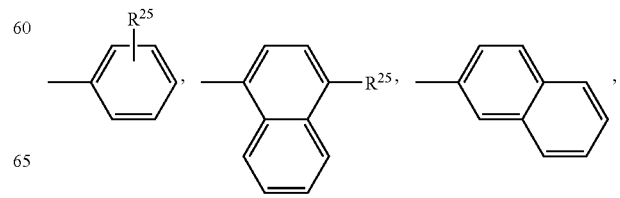

-continued
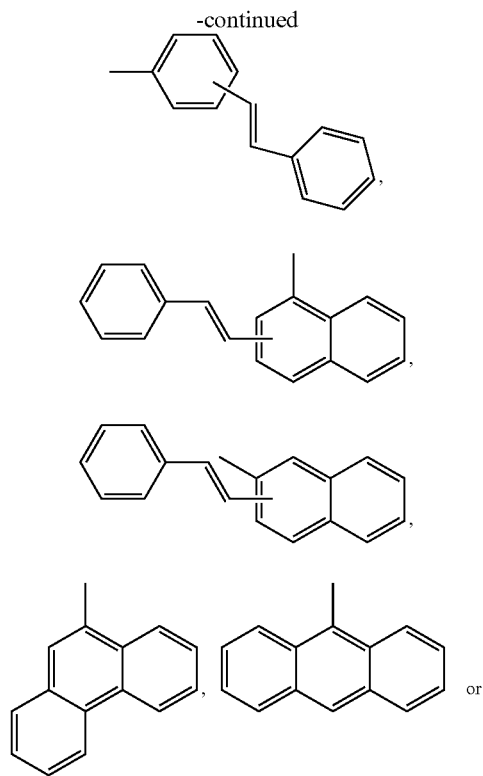
wherein R²⁵ is C₁-C₈-alkyl, phenyl, 1- or 2-naphthyl.
12. A composition according to claim 11, wherein the host chromophore is a diketopyrrolopyrrole represented by formula II, wherein A⁴ and A⁵ independently from each other stand for
wherein R²⁵ is C₁-C₈-alkyl
and the guest chromophore is a fluorescent diketopyrrolopyrrole selected from
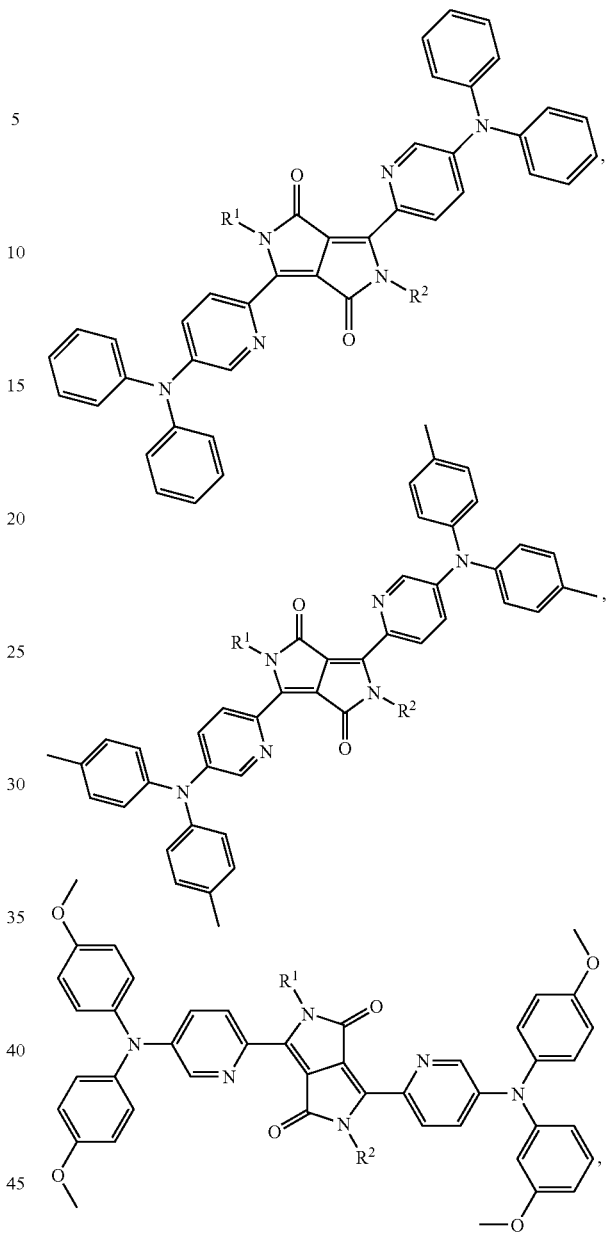

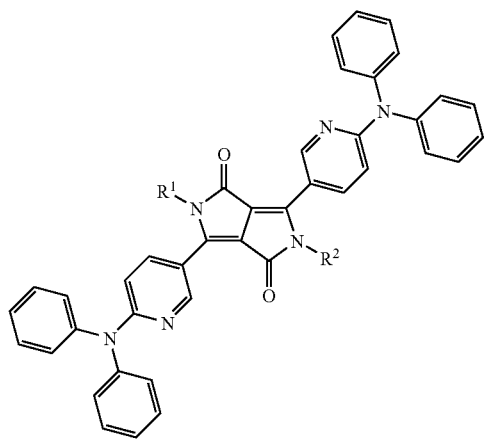
and
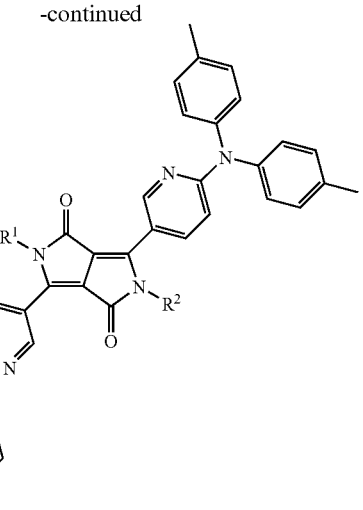
wherein $R^1$ and $R^2$ are independently of each other a $C_1$-$C_{12}$alkyl group.
* * * * *